United States Patent
Seward et al.

(10) Patent No.: US 11,654,267 B2
(45) Date of Patent: May 23, 2023

(54) MEDICAL INSTRUMENT AND MEDICAL METHOD FOR LOCALIZED DRUG DELIVERY

(71) Applicant: Mercator MedSystems, Inc., Emeryville, CA (US)

(72) Inventors: Kirk P. Seward, San Francisco, CA (US); David Gandionco, San Francisco, CA (US); Amy Skarsfeldt, Allerod (DK); Alexandra Knauer, Mill Valley, CA (US)

(73) Assignee: MERCATOR MEDSYSTEMS, INC., Emeryville, CA (US)

( * ) Notice: Subject to any disclaimer, the term of this patent is extended or adjusted under 35 U.S.C. 154(b) by 156 days.

(21) Appl. No.: 16/977,355

(22) PCT Filed: Mar. 13, 2019

(86) PCT No.: PCT/US2019/022054
§ 371 (c)(1),
(2) Date: Sep. 1, 2020

(87) PCT Pub. No.: WO2019/178228
PCT Pub. Date: Sep. 19, 2019

(65) Prior Publication Data
US 2021/0106793 A1    Apr. 15, 2021

Related U.S. Application Data

(60) Provisional application No. 62/642,743, filed on Mar. 14, 2018.

(51) Int. Cl.
*A61M 25/10*    (2013.01)
*A61M 25/00*    (2006.01)
(Continued)

(52) U.S. Cl.
CPC ........ *A61M 25/10* (2013.01); *A61M 25/0009* (2013.01); *A61M 25/0097* (2013.01);
(Continued)

(58) Field of Classification Search
CPC .. A61M 2025/1004; A61M 2025/0092; A61M 25/0052; A61M 2025/1031;
(Continued)

(56) References Cited

U.S. PATENT DOCUMENTS 4,651,721 A    3/1987  Mikulich et al.
5,009,659 A    4/1991  Hamlin et al.
(Continued)

FOREIGN PATENT DOCUMENTS

CN    1726884 A      2/2006
CN    103284948 A    9/2013
(Continued)

OTHER PUBLICATIONS

Altman et al., Exploring heart lymphatics in local drug delivery, Lymph. Res. Biol., (2003) 1:47-54.
(Continued)

*Primary Examiner* — Brandy S Lee
*Assistant Examiner* — John J Crawford
(74) *Attorney, Agent, or Firm* — Wilson Sonsini Goodrich & Rosati

(57) ABSTRACT

Disclosed herein are medical instrument and medical method for localized drug delivery. The medical instrument can comprise a catheter shaft assembly, a hub coupled to the proximal end of the catheter shaft assembly, an inflatable component at the distal end of the catheter shaft assembly, a tissue penetrating member coupled to the inflatable component in an orientation transverse to the longitudinal axis of the catheter shaft assembly, and at least one protective element coupled to the inflatable component in proximity to
(Continued)

the tissue penetrating member. The protective element can be configured to prevent any damage of the inflatable body during a placement of the medical instrument and an actuation of the inflatable component.

28 Claims, 12 Drawing Sheets

(51) Int. Cl.
*A61M 25/01* (2006.01)
*A61M 39/24* (2006.01)

(52) U.S. Cl.
CPC .... *A61M 25/0108* (2013.01); *A61M 25/0155* (2013.01); *A61M 39/24* (2013.01); *A61M 2205/3331* (2013.01); *A61M 2205/60* (2013.01)

(58) Field of Classification Search
CPC .. A61M 2025/1079; A61M 2025/1086; A61M 25/0138
See application file for complete search history.

(56) References Cited

U.S. PATENT DOCUMENTS

| | | |
|---|---|---|
| 5,078,725 A | 1/1992 | Enderle et al. |
| 5,112,305 A | 5/1992 | Barath et al. |
| 5,196,024 A | 3/1993 | Barath |
| 5,270,047 A | 12/1993 | Kauffman et al. |
| 5,354,279 A | 10/1994 | Hoefling |
| 5,362,718 A | 11/1994 | Skotnicki et al. |
| 5,527,532 A | 6/1996 | Edelman et al. |
| 5,538,504 A | 7/1996 | Linden et al. |
| 5,562,620 A | 10/1996 | Klein et al. |
| 5,645,564 A | 7/1997 | Northrup et al. |
| 5,681,281 A | 10/1997 | Vigil et al. |
| 5,693,029 A | 12/1997 | Leonhardt |
| 5,713,913 A * | 2/1998 | Lary ............... A61M 25/10 604/103.1 |
| 5,722,989 A | 3/1998 | Fitch et al. |
| 5,749,851 A | 5/1998 | Wang et al. |
| 5,866,561 A | 2/1999 | Ungs |
| 5,900,246 A | 5/1999 | Lambert |
| 6,009,877 A | 1/2000 | Edwards |
| 6,059,815 A | 5/2000 | Lee et al. |
| 6,102,904 A | 8/2000 | Vigil et al. |
| 6,102,933 A | 8/2000 | Lee et al. |
| 6,210,392 B1 | 4/2001 | Vigil et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,334,856 B1 | 1/2002 | Allen et al. |
| 6,494,862 B1 | 12/2002 | Ray et al. |
| 6,527,741 B1 | 3/2003 | Lee et al. |
| 6,547,303 B1 | 4/2003 | Anderson |
| 6,547,803 B2 | 4/2003 | Seward et al. |
| 6,625,486 B2 | 9/2003 | Lundkvist et al. |
| 6,660,024 B1 | 12/2003 | Flaherty et al. |
| 6,860,867 B2 | 3/2005 | Seward et al. |
| 6,872,215 B2 | 3/2005 | Crocker et al. |
| 7,008,411 B1 | 3/2006 | Mandrusov et al. |
| 7,094,765 B1 | 8/2006 | Iversen et al. |
| 7,141,041 B2 | 11/2006 | Seward |
| 7,247,149 B2 | 7/2007 | Beyerlein |
| 7,338,463 B2 | 3/2008 | Vigil |
| 7,413,558 B2 | 8/2008 | Kelley et al. |
| 7,691,080 B2 | 4/2010 | Seward et al. |
| 7,744,584 B2 | 6/2010 | Seward et al. |
| 8,016,786 B2 | 9/2011 | Seward et al. |
| 8,066,726 B2 * | 11/2011 | Kelley ........... A61B 17/320725 606/159 |
| 8,708,995 B2 | 4/2014 | Seward et al. |
| 8,721,590 B2 | 5/2014 | Seward et al. |
| 9,061,098 B2 | 6/2015 | Seward et al. |
| 9,220,716 B2 | 12/2015 | Bischoff et al. |
| 9,248,256 B2 | 2/2016 | Takagi et al. |
| 9,789,276 B2 | 10/2017 | Seward et al. |
| 9,884,013 B2 | 2/2018 | Seward et al. |
| 10,441,747 B2 | 10/2019 | Kirk |
| 10,561,816 B2 | 2/2020 | Seward et al. |
| 10,576,063 B2 | 3/2020 | Seward |
| 10,617,678 B2 | 4/2020 | Kirk |
| 2002/0001581 A1 | 1/2002 | Lynch et al. |
| 2002/0052404 A1 | 5/2002 | Hunter et al. |
| 2002/0072755 A1 | 6/2002 | Bigus et al. |
| 2002/0156000 A1 | 10/2002 | May et al. |
| 2002/0188310 A1 | 12/2002 | Seward et al. |
| 2003/0040712 A1 | 2/2003 | Ray et al. |
| 2003/0055400 A1 | 3/2003 | Seward et al. |
| 2003/0055446 A1 | 3/2003 | Seward et al. |
| 2003/0078562 A1 | 4/2003 | Makower et al. |
| 2003/0120297 A1 | 6/2003 | Beyerlein |
| 2003/0170287 A1 | 9/2003 | Prescott |
| 2003/0171734 A1 | 9/2003 | Seward et al. |
| 2004/0067197 A1 | 4/2004 | Leclerc et al. |
| 2004/0138643 A1 | 7/2004 | Seward et al. |
| 2004/0162542 A1 | 8/2004 | Wilber et al. |
| 2004/0167152 A1 | 8/2004 | Rubino et al. |
| 2004/0181206 A1 * | 9/2004 | Chiu .................... A61M 25/10 604/509 |
| 2004/0188203 A1 | 9/2004 | Gold et al. |
| 2004/0260240 A1 | 12/2004 | Beyerlein |
| 2004/0260268 A1 | 12/2004 | Falotico et al. |
| 2005/0033225 A1 | 2/2005 | Wu et al. |
| 2005/0090714 A1 | 4/2005 | Greff |
| 2005/0137616 A1 * | 6/2005 | Vigil ............. A61B 17/320725 606/170 |
| 2005/0137617 A1 | 6/2005 | Kelley et al. |
| 2005/0158361 A1 | 7/2005 | Dhondt et al. |
| 2005/0163711 A1 | 7/2005 | Nycz et al. |
| 2005/0182071 A1 | 8/2005 | Seward et al. |
| 2005/0232965 A1 | 10/2005 | Falotico |
| 2005/0245862 A1 * | 11/2005 | Seward ............. A61M 25/0133 604/95.04 |
| 2006/0069349 A1 | 3/2006 | Ganz et al. |
| 2006/0115903 A1 | 6/2006 | Ridker et al. |
| 2006/0122684 A1 | 6/2006 | Lye et al. |
| 2006/0189941 A1 | 8/2006 | Seward et al. |
| 2007/0078620 A1 | 4/2007 | Seward et al. |
| 2007/0100318 A1 | 5/2007 | Seward et al. |
| 2007/0100319 A1 | 5/2007 | Seward et al. |
| 2007/0100320 A1 | 5/2007 | Seward et al. |
| 2007/0106248 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106252 A1 | 5/2007 | Seward et al. |
| 2007/0106253 A1 | 5/2007 | Seward et al. |
| 2007/0106254 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0129706 A1 * | 6/2007 | Katoh ............... A61M 25/0071 604/525 |
| 2007/0129789 A1 | 6/2007 | Cottone, Jr. et al. |
| 2007/0269385 A1 | 11/2007 | Yun et al. |
| 2008/0038316 A1 | 2/2008 | Wong et al. |
| 2008/0228136 A1 * | 9/2008 | Seward ............. A61M 25/0012 604/96.01 |
| 2009/0204104 A1 | 8/2009 | Tremble et al. |
| 2010/0063479 A1 * | 3/2010 | Merdan ................. A61M 25/09 604/528 |
| 2010/0082095 A1 | 4/2010 | Pacetti et al. |
| 2010/0092534 A1 | 4/2010 | Hezi-Yamit et al. |
| 2010/0145307 A1 | 6/2010 | Seward et al. |
| 2010/0152702 A1 | 6/2010 | Vigil et al. |
| 2010/0292641 A1 | 11/2010 | Wijay et al. |
| 2010/0305546 A1 | 12/2010 | Seward et al. |
| 2010/0330147 A1 | 12/2010 | Hossainy et al. |
| 2011/0313353 A1 | 12/2011 | Seward et al. |
| 2013/0029950 A1 | 1/2013 | Bischoff et al. |
| 2013/0035665 A1 | 2/2013 | Chu et al. |

(56) References Cited

U.S. PATENT DOCUMENTS

| | | |
|---|---|---|
| 2013/0204131 A1 | 8/2013 | Seward |
| 2013/0224255 A1 | 8/2013 | Hossainy et al. |
| 2014/0107478 A1 | 4/2014 | Seward et al. |
| 2014/0275777 A1* | 9/2014 | Gunday ......... A61B 17/320725 600/109 |
| 2014/0296279 A1 | 10/2014 | Seward et al. |
| 2015/0100040 A1 | 4/2015 | Kobayashi et al. |
| 2016/0271116 A1 | 9/2016 | Jia et al. |

FOREIGN PATENT DOCUMENTS

| | | |
|---|---|---|
| JP | 2000511161 A | 8/2000 |
| JP | 2005349202 A | 12/2005 |
| JP | 2014523267 A | 9/2014 |
| WO | WO-0112255 A1 | 2/2001 |
| WO | WO-0121157 A2 | 3/2001 |
| WO | WO-0121157 A3 | 12/2001 |
| WO | WO-02055130 A2 | 7/2002 |
| WO | WO-2004011000 A1 | 2/2004 |
| WO | WO-2004098681 A1 | 11/2004 |
| WO | WO-2007120897 A2 | 10/2007 |
| WO | WO-2010104584 A2 | 9/2010 |
| WO | WO-2012149451 A1 | 11/2012 |
| WO | WO-2014118696 A2 | 8/2014 |
| WO | WO-2017078405 A1 | 5/2017 |
| WO | WO-2018218182 A1 | 11/2018 |

OTHER PUBLICATIONS

Ayers et al., Amiodarone instilled into the canine pericardial sac migrates transmurally to produce electrophysiologic effects and suppress atrial fibrillation. Journal of Cardiovascular Electrophysiology. 7(8):713-721 (1996).

Barath et al., "Infiltrator Angioplasty Balloon Catheter: a device for combined angioplasty and intramural site-specific treatment," Cathet Cardiovasc Diagn. Jul. 1997;41(3):333-341.

Bruun et al., Monocyte chemoattractant protein-1 release is higher in visceral than subcutaneous human adipose tissue (AT): implication of macrophages resident in the AT. The Journal of Clinical Endocrinology and Metabolism 90(4):2282-2289 (2005).

Chandrasekar et al., "Coronary Artery Endothelial. Protection After Local Delivery of 1711-Estradiol During Balloon Angioplasty in a Porcine Model : A Potential New Pharmacologic Approach to Improve Endothelial Function," J. Am. Col. Cardiol. (2001), 38(5):1570-1576.

Chandrasekar et al., "Local Delivery of 17-Beta-Estradiol Decreases Neointimal Hyperplasia After Coronary Angioplasty in a Porcine Model," J. Am. Col. Cardiol. (2000), 36(6):1972-1978.

Cipollone et al., Elevated circulating levels of monocyte chemoattractant protein-1 in patients with restenosis after coronary angioplasty. Arterioscler Thromb Vase Biol. 21(3):327-334 (2001).

ClinicalTrials.gov. Identifier: NCT01507558. Dexamethasone Infusion to the Adventitia to Enhance Clinical Efficacy After Femoropopliteal Revascularization (DANCE). https://clinicaltrials.gov/ct2/show/NCT01507558?term=nct01507558&rank=1. Last updated Aug. 15, 2014. Accessed on Mar. 4, 2015. 4 pages.

Creel, "Arterial Paclitaxel Distribution and Deposition," Circulation Research. Apr. 2000;86:879-884.

Dai-Do et al., "17 beta-estradiol inhibits proliferation and migration of human vascular smooth muscle cells: similar effects in cells from postmenopausal females and in males," Cardiovasc Res. Nov. 1996;32(5):980-985.

Daschner et al., Penetration of gentamicin into heart valves, subcutaneous and muscular tissue of patients undergoing open heart surgery, J. Cardiovasc. Surg., (1986) 581-584.

Declaration of Kirk Patrick Seward in U.S. Appl. No. 14/605,865 dated Mar. 1, 2019.

Franchimont et al., Tumor necrosis factor alpha decreases, and interleukin-10 increases, the sensitivity of human monocytes to dexamethasone: potential regulation of the glucocorticoid receptor. J Clin Endocrinol Metab. 84(8):2834-2839 (1999).

Gaspardone, et al. C-Reactive protein, clinical outcome, and restenosis rates after implantation of different drug-eluting stents. Am J Cardiol. May 1, 2006;97(9):1311-6. Epub Mar. 20, 2006.

Gasper, W. et al. Adventitial Nab-Rapamycin Injection Reduces Porcine Femoral Artery Luminal Stenosis Induced by Balloon Angioplasty via Inhibition of Medial Proliferation and Adventitial Inflammation. Circulation: Cardiovascular Interventions. 6(6):701-709 (Dec. 1, 2013).

Greenberger et al., Rapamycin Suppresses Self-Renewal and Vasculogenic Potential of Stem Cells Isolated from Infantile Hemangioma. Journal of Investigative Dermatology 131: 2467-2476 (2011).

Han, et al. The favorable clinical and angiographic outcomes of a high-dose dexamethasone-eluting stent: randomized controlled prospective study. Am Heart J. Nov. 2006;152(5):887.e1-7.

Heider et al., Role of adhesion molecules in the induction of restenosis after angioplasty in the lower limb. Journal of Vascular Surgery 43(5):969-977 (2006).

Ikeno et al., "Novel percutaneous adventitial drug delivery system for regional vascular treatment," Catheter Cardiovasc. interv., (2004) 63: 220-230.

International Application No. PCT/US17/52790 International Search Report and Written Opinion dated Dec. 8, 2017.

International Application No. PCT/US18/34713 Search Report and Written Opinion dated Oct. 19, 2018.

International search report and written opinion dated Mar. 17, 2016 for PCT/US2016/014819.

International search report and written opinion dated Sep. 15, 2008 for PCT/US2007/079163.

International search report dated Apr. 21, 2004 for PCT/US2003/002130.

Konig, et al. Randomized comparison of dexamethasone-eluting stents with bare metal stent implantation in patients with acute coronary syndrome: serial angiographic and sonographic analysis. Am Heart J. Jun. 2007;153(6):979.e1-8.

Laham et al., Intracoronary and intravenous administration of basic fibroblast growth factor: myocardial and tissue distribution, Drug Met. Disp., (1999) 27:821-826.

Laham et al., Intrapericardial administration of basic fibroblast growth factor: myocardial and tissue distribution and comparison with intracoronary and intravenous administration, Cath Cardio. Interv., (2003) 58:375-381.

Libby et al., Inflammation in atherosclerosis. Arteriosclerosis, Thrombosis and Vascular Biology 32(9):2045-2051 (2012).

Moreno, Drug-Eluting Stents and Other Anti-Restenosis Devices. Rev Esp Cardiol 58(7): 842-862 (2005).

Nikol et al., Needle injection catheter delivery of the gene for an antibacterial agent inhibits neointimal formation. Gene Therapy 6(5):737-748 (1999).

Office action dated Jan. 9, 2015 for U.S. Appl. No. 14/203,942.
Office action dated Jan. 10, 2013 for U.S. Appl. No. 13/222,977.
Office action dated Jan. 30, 2007 for U.S. Appl. No. 10/350,314.
Office action dated Feb. 2, 2011 for U.S. Appl. No. 12/790,541.
Office action dated Feb. 5, 2009 for U.S. Appl. No. 11/858,797.
Office action dated Feb. 26, 2009 for U.S. Appl. No. 10/691,119.
Office action dated Apr. 16, 2008 for U.S. Appl. No. 10/691,119.
Office Action dated Apr. 24, 2019 U.S. Appl. No. 15/691,138.
Office action dated May 15, 2008 for U.S. Appl. No. 10/350,314.
Office action dated May 16, 2007 for U.S. Appl. No. 10/350,314.
Office action dated May 28, 2009 for U.S. Appl. No. 11/858,797.
Office action dated Jun. 25, 2007 for U.S. Appl. No. 11/601,290.
Office action dated Jun. 25, 2007 for U.S. Appl. No. 11/607,177.
Office action dated Jun. 27, 2007 for U.S. Appl. No. 11/607,168.
Office action dated Jun. 27, 2007 for U.S. Appl. No. 11/607,170.
Office action dated Jun. 27, 2007 for U.S. Appl. No. 11/607,172.
Office action dated Jun. 27, 2007 for U.S. Appl. No. 11/607,175.
Office action dated Jun. 27, 2007 for U.S. Appl. No. 11/607,176.
Office action dated Jun. 27, 2007 for U.S. Appl. No. 11/607,356.
Office action dated Jul. 2, 2007 for U.S. Appl. No. 11/607,355.
Office action dated Jul. 12, 2013 for U.S. Appl. No. 13/222,977.
Office action dated Jul. 14, 2006 for U.S. Appl. No. 10/350,314.

(56) References Cited

OTHER PUBLICATIONS

Office action dated Jul. 16, 2007 for U.S. Appl. No. 11/607,166.
Office action dated Jul. 16, 2007 for U.S. Appl. No. 11/607,167.
Office action dated Jul. 16, 2007 for U.S. Appl. No. 11/607,178.
Office action dated Jul. 16, 2007 for U.S. Appl. No. 11/607,658.
Office action dated Jul. 17, 2007 for U.S. Appl. No. 11/607,169.
Office action dated Aug. 20, 2008 for U.S. Appl. No. 10/350,314.
Office action dated Aug. 20, 2008 for U.S. Appl. No. 10/691,119.
Office action dated Aug. 24, 2007 for U.S. Appl. No. 10/350,314.
Office action dated Sep. 15, 2009 for U.S. Appl. No. 10/691,119.
Office action dated Oct. 11, 2011 for U.S. Appl. No. 12/790,541.
Office action dated Dec. 12, 2006 for U.S. Appl. No. 10/691,119.
Owens, Christopher D., MD. Pilot Results from DANCE: Dexamethasone to the Adventitia to eNhance Clinical Efficacy in PAD. pp. 1-19 (2012).
Owens et al., Safety and feasibility of adjunctive dexamethasone infusion into the adventitia of the femoropopliteal artery following endovascular revascularization. Journal of Vascular Surgery. 59(4):1016-1024 (2014).
PCT/US2018/034713 International Preliminary Report on Patentability dated Nov. 26, 2019.
PCT/US2019/022054 International Search Report and Written Opinion dated May 30, 2019.
Pharmacia & Upjohn Company, "Depo-Estradiol," Product/Prescription Information [pamphlet], (Aug. 2000), 6 pages total.
Ross et al., The pathogenesis of atherosclerosis. New England Journal of Medicine 295(7-8):369-377, 420-425 (1976).
Schillinger, et al. Balloon angioplasty and stent implantation induce a vascular inflammatory reaction. J Endovasc Ther. Feb. 2002;9(1):59-66.
Siablis, D. et al. Sirolimus-Eluting Versus Bare Stents After Suboptimal Ingrapopliteal Angioplastry for Critical Limb Ischemia: Enduring 1-Year Angiographic and Clinical Benefit, J. Endovasc. Ther. 14:241-250 (2007).
Solomon et al., Amiodarone versus a beta-blocker to prevent atrial fibrillation after cardiovascular surgery. American Heart Journal 142(5):811-815 (2001).
U.S. Appl. No. 16/058,690 Office Action dated Aug. 7, 2019.
U.S. Appl. No. 14/063,604 Final Office Action dated Feb. 14, 2017.
U.S. Appl. No. 14/063,604 Non-Final Office Action dated Jun. 15, 2016.
U.S. Appl. No. 14/603,604 Final Office Action dated Jan. 21, 2016.
U.S. Appl. No. 14/603,604 Non-Final Office Action dated May 29, 2015.
U.S. Appl. No. 14/605,865 Final Office Action dated Aug. 31, 2017.
U.S. Appl. No. 14/605,865 Non-Final Office Action dated Dec. 28, 2017.
U.S. Appl. No. 14/605,865 Non-Final Office Action dated Sep. 17, 2018.
U.S. Appl. No. 14/605,865 Office Action dated Sep. 22, 2016.
U.S. Appl. No. 15/890,857 Final Office Action dated Nov. 14, 2018.
U.S. Appl. No. 15/890,857 Non-Final Office Action dated May 30, 2018.
U.S. Appl. No. 16/058,690 Final Office Action dated Oct. 13, 2020.
U.S. Appl. No. 15/890,857 Office Action dated Jul. 1, 2019.
U.S. Appl. No. 16/591,467 Non-Final Office Action dated Apr. 27, 2020.
U.S. Appl. No. 15/990,167 Office Action dated Apr. 10, 2019.
Wildgruber et al., Early endothelial and haematological response to cryoplasty compared with balloon angioplasty of the superficial femoral artery—a pilot study. The British Journal of Radiology 80(954):430-436 (2007).
Zhang et al. Synergistic activity of rapamycin and dexamethasone in vitro and in vivo in acute lymphoblastic leukemia via cell-cycle arrest and apoptosis. Leukemia Research 36(3):342-349 (2012).
Zhou et al., Dexamethasone suppresses monocyte chemoattractant protein-1 production via mitogen activated protein kinase phosphatase-1 dependent inhibition of Jun N-terminal kinase and p38 mitogen-activated protein kinase in activated rat microglia. J Neurochem 102(3): 667-678 (2007).

\* cited by examiner

MEDICAL INSTRUMENT AND MEDICAL METHOD FOR LOCALIZED DRUG DELIVERY

CROSS-REFERENCE TO RELATED APPLICATIONS

The present application is a § 371 U.S. National Stage Entry of International Application No. PCT/US2019/022054, filed Mar. 13, 2019, which claims the benefit of U.S. Application No. 62/642,743, filed Mar. 14, 2018, entitled "DEVICE FOR INTRAVASCULAR LOCAL DRUG DELIVERY", the entire contents of which are incorporated herein by reference.

The subject matter of the present application is related to the subject matter of U.S. application Ser. No. 10/350,314, filed on Jan. 22, 2003, entitled "METHODS AND KITS FOR DELIVERING PHARMACEUTICAL AGENTS INTO THE CORONARY VASCULAR ADVENTITIA", U.S. application Ser. No. 10/691,119, filed on Oct. 21, 2003, entitled "METHODS AND KITS FOR VOLUMETRIC DISTRIBUTION OF PHARMACEUTICAL AGENTS VIA THE VASCULAR ADVENTITIA AND MICROCIRCULATION", U.S. application Ser. No. 12/790,541, filed on May 28, 2010, entitled "METHODS AND KITS FOR VOLUMETRIC DISTRIBUTION OF PHARMACEUTICAL AGENTS VIA THE VASCULAR ADVENTITIA AND MICROCIRCULATION", U.S. application Ser. No. 14/203,942, filed on Mar. 11, 2014, entitled "METHODS AND KITS FOR VOLUMETRIC DISTRIBUTION OF PHARMACEUTICAL AGENTS VIA THE VASCULAR ADVENTITIA AND MICROCIRCULATION", U.S. application Ser. No. 14/605,865, filed on Jan. 26, 2015, entitled "METHODS AND SYSTEMS FOR INHIBITING VASCULAR INFLAMMATION", PCT/US16/14819, filed Jan. 26, 2017, entitled "METHODS AND SYSTEMS FOR INHIBITING VASCULAR INFLAMMATION", U.S. application Ser. No. 11/858,797, filed on Sep. 20, 2007, entitled "DUAL MODULUS BALLOON FOR INTERVENTIONAL PROCEDURES", U.S. application Ser. No. 12/711,141, filed on Feb. 23, 2010, entitled "DUAL MODULUS BALLOON FOR INTERVENTIONAL PROCEDURES", U.S. application Ser. No. 13/222,977, filed on Aug. 31, 2011, entitled "DUAL MODULUS BALLOON FOR INTERVENTIONAL PROCEDURES" U.S. application Ser. No. 14/063,604, filed on Oct. 25, 2013, entitled "DUAL MODULUS BALLOON FOR INTERVENTIONAL PROCEDURES" U.S. application Ser. No. 15/691,138, filed on Aug. 30, 2017, entitled "DUAL MODULUS BALLOON FOR INTERVENTIONAL PROCEDURES", and PCT/US07/79163, filed Sep. 21, 2017, entitled "DUAL MODULUS BALLOON FOR INTERVENTIONAL PROCEDURES"; the entire contents of which are incorporated herein by reference.

BACKGROUND

The present disclosure relates generally to medical devices and medical methods. More particularly, the present disclosure relates to medical instruments and medical methods for localized drug delivery to a patient's tissue.

Percutaneous or endoscopic interventional procedures are common in the United States and other countries around the world. Intravascular catheter systems are used for procedures such as balloon angioplasty, stent placement, atherectomy, retrieval of blood clots, photodynamic therapy, and drug delivery. These procedures typically involve the placement of long, slender tubes known as catheters into arteries, veins, or other lumens of the body in order to provide access to the deep recesses of the body without the necessity of open surgery.

Medical devices used in catheter-based procedures often include a working component at or near the distal (e.g., farthest from the operator) end of the catheter that is operated by hydraulic, pneumatic, or other mechanical means. These systems can sometimes include a working component such as microneedle(s) at the distal end of the catheter that can be opposed against the wall of the lumen, for example, to provide localized injection of a drug or other agent or substance. Such catheters can also benefit the treatment of other lumens in the body. For example, the sinus passages leading from nasal openings to the sinuses or pharynx may become inflamed, for example, after sinus surgery or in the case of nasal polyposis. In these cases, systems similar to those used in percutaneous procedures may also require apposition of one side of the working end against the lumen wall.

Catheters carrying microneedles capable of delivering therapeutic and other agents deep into a layer surrounding lumens of the body have been developed. In many cases, the microneedles are delivered in a direction which is substantially perpendicular to the axis of the catheter, thus maximizing the depth of needle penetration into the lumen wall and reducing trauma and injury. The needles can be carried on an expansible surface structure such as hydraulic actuating balloon to accommodate various lumen sizes. Moreover, by locating the needles on the exterior of an expansible surface structure, the needles can be injected into tissue fully up to their point of attachment to the catheter, further increasing the needle penetration depth which may be achieved. However, the routing of fluids through catheter tubing and into needles in the case in which the needles are actuated by a hydraulic balloon leads to design complexity requiring solutions for focally sealing tubings to keep drug and activation fluids separate. Moreover, in the cases where guidewires are used to place catheters, a guidewire access tube is required to be incorporated into the balloon structure and must also be sealed apart from the drug and activation fluids.

SUMMARY

It would be desirable to provide improved catheters carrying needles on a balloon or other inflation structure where the balloon or other inflation structure is protected during a placement of the catheter and an actuation of the balloon. For instance, the balloon may be subject to damage by the sharp needle end during an expansion of the balloon. It is a further objective that an indicator can be provided to catheters to indicate a position of the catheter and/or expansion status of the balloon or other inflation structure on which needles are carried. It is a further objective that catheter devices be torqueable in a way that rotation of the devices at the user end (often outside of the body) leads to a predictable rotation of the device at the working end (often well inside the body) to provide for accurate needle placement. It is a further objective that three lumens are provided for the transit of guidewire, activation fluid, and drug, and that these three lumens remain separate throughout the catheter tubing and all interconnections.

An aspect of the present disclosure provides a medical instrument for localized drug delivery to tissue. The medical instrument can comprise a catheter shaft assembly having a proximal end, a distal end, a longitudinal axis between the proximal and distal ends, at least one injection lumen, at least one inflation lumen, and a guidewire lumen; a hub coupled to the proximal end of the catheter shaft assembly, the hub comprising at least one injection port coupled to the at least one injection lumen, at least one inflation port coupled to the at least one inflation lumen, and a guidewire port coupled to the guidewire lumen; an inflatable body at the distal end of the catheter shaft assembly, the inflatable body being inflatable from an involuted contracted configuration; a tissue penetrating member coupled to the inflatable body in an orientation transverse to the longitudinal axis of the catheter shaft assembly and further coupled to an injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; and at least one protective element coupled to the inflatable body in proximity to the tissue penetrating member, at least the tip end of the tissue penetrating member being bordered by the at least one protective element when the inflatable body is in the involuted contracted configuration.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

Another aspect of the present disclosure provides a method for delivering a drug to a patient. The method can comprise providing a medical instrument according to embodiments of the present disclosure; advancing the medical instrument over a guidewire to a predetermined position within a body lumen of the patient when the inflatable body is in the involuted contracted configuration; inflating the inflatable body when the catheter shaft assembly is at the predetermined position in the body lumen; and delivering the drug to the patient through the tissue penetrating member, where the tissue penetrating member is in fluid communication with a drug lumen.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

Another aspect of the present disclosure provides a method of manufacturing a medical instrument for localized drug delivery to tissue. The method can comprise providing a catheter shaft assembly having a proximal end, a distal end, a longitudinal axis between the proximal and distal ends, at least one injection lumen, at least one inflation lumen, and a guidewire lumen; coupling a hub to the proximal end of the catheter shaft assembly, the hub comprising an injection port coupled to the at least one injection lumen, an inflation port coupled to the at least one inflation lumen, and a guidewire port coupled to the guidewire lumen; coupling an inflatable body at the distal end of the catheter shaft assembly, the inflatable body being inflatable from an involuted contracted configuration; coupling a tissue penetrating member to the inflatable body in an orientation transverse to the longitudinal axis of the catheter shaft assembly, and further coupling the tissue penetrating member to an injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; and coupling at least one protective element to the inflatable body in proximity to the tissue penetrating member, at least the tip end of the tissue penetrating member being bordered by the at least one protective element when the inflatable body is in the involuted contracted configuration.

In some embodiments, the injection port, the inflation port and the guidewire port can be Luer interface. The inflation port can be coupled to a pressure release valve configured to regulate a pressure of a hydraulic fluid. In some embodiments, the method can further comprise attaching a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the method can further comprise providing a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

In some embodiments, the method can further comprise coupling a fluid routing tube along an exterior of the wall of the inflatable body by means of an elastomer coated with parylene. In some embodiments, the body lumen can be a blood vessel. The body lumen can be a peripheral blood vessel. In some instances, inflating the inflatable body can advances the tip of the tissue penetrating element beyond external elastic lamina (EEL) of a blood vessel. In some instances, inflating the inflatable body can contact the inflatable body against inner wall of body lumen.

In some embodiments, inflating the inflatable body can comprise inflating to a first expanded configuration and then inflating to the inflatable body to a second expanded configuration larger than the first expanded configuration. In some instances, the inflatable body can comprise a first section with a first elasticity and a second section with a second elasticity such that the inflatable body is inflatable from the involuted contracted configuration to the first expanded configuration and further inflatable from the first expanded configuration to the second expanded configuration In some embodiments, inflating the inflatable body can change an orientation of the at least one protective element. The method can further comprise observing the orientation change of the at least one protective element to confirm inflation of the inflatable body. In some embodiments, delivering the drug to the patient can comprise providing drug through the injection port of the hub.

Another aspect of the present disclosure provides a medical instrument for localized drug delivery to tissue. The medical instrument can comprise a catheter shaft assembly having a proximal end, a distal end, a longitudinal axis between the proximal and distal ends, at least one injection lumen, and at least one inflation lumen; a hub coupled to the proximal end of the catheter shaft assembly, the hub comprising an injection port coupled to the at least one injection lumen and an inflation port coupled to the at least one inflation lumen; an inflatable body at the distal end of the catheter shaft assembly, the inflatable body being inflatable from an involuted contracted configuration; a tissue penetrating member coupled to the inflatable body in an orientation transverse to the longitudinal axis of the catheter shaft assembly and further coupled to the at least one injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; a torque transmission member coupled to one or more of the distal end of the catheter shaft assembly or the inflatable body; a torqueing element adjacent the proximal end of the catheter shaft assembly and coupled to the torque transmission member to transmit torque applied to the torqueing element to one or more of the distal end of the catheter shaft assembly or the inflatable body; and at least one protective element coupled to the first section in proximity to the tissue penetrating member, at least the tip end of the tissue penetrating member being bordered by the at least one protective element when the inflatable body is in the involuted contracted configuration.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the tissue penetrating member can be coupled to the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a guidewire lumen and the hub further comprises a guidewire port coupled to the guidewire lumen. The guidewire port can be a Luer interface.

Another aspect of the present disclosure provides a method for delivering a drug to a patient. The method can comprise providing a medical instrument according to embodiments of the present disclosure; advancing the medical instrument to a predetermined position within a body lumen of the patient when the inflatable body is in the involuted contracted configuration; torquing the medical instrument with the torqueing element; inflating the inflatable body when the catheter is at the predetermined position in the body lumen; and delivering the drug to the patient through the tissue penetrating member, where the tissue penetrating member is in fluid communication with a drug lumen.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the tissue penetrating member can be coupled to the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a guidewire lumen and the hub further comprises a guidewire port coupled to the guidewire lumen. The guidewire port can be a Luer interface.

Another aspect of the present disclosure provides a method of manufacturing medical instrument for localized drug delivery to tissue. The method can comprise providing a catheter shaft assembly having a proximal end, a distal end, a longitudinal axis between the proximal and distal ends, at least one injection lumen, and at least one inflation lumen; coupling a hub to the proximal end of the catheter shaft assembly, the hub comprising an injection port coupled to the at least one injection lumen and an inflation port coupled to the at least one inflation lumen; coupling an inflatable body at the distal end of the catheter shaft assembly, the inflatable body being inflatable from an involuted contracted configuration; coupling a tissue penetrating member to the inflatable body in a orientation transverse to the longitudinal axis of the catheter shaft assembly, and further coupling the tissue penetrating member to the injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; coupling a torque transmission member to one or more of the distal end of the catheter shaft assembly or the inflatable body; providing a torqueing element adjacent the proximal end of the catheter shaft assembly and coupling the torqueing element to the torque transmission member to transmit torque applied to the torqueing element to one or more of the distal end of the catheter shaft assembly or the inflatable body; and coupling at least one protective element to the first section in proximity to the tissue penetrating member, at least the tip end of the tissue penetrating member being bordered by the at least one protective element when the inflatable body is in the involuted contracted configuration.

In some embodiments, the injection port, the inflation port and the guidewire port can be Luer interface. The inflation port can be coupled to a pressure release valve configured to regulate a pressure of a hydraulic fluid. In some embodiments, the method can further comprise attaching a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the tissue penetrating member can be coupled to the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the method can further comprise providing a guidewire lumen and the hub further comprises a guidewire port coupled to the guidewire lumen. The guidewire port can be a Luer interface.

In some embodiments, the method can further comprise coupling a fluid routing tube along an exterior of the wall of the inflatable body by means of an elastomer coated with parylene. In some embodiments, the body lumen can be a blood vessel. The body lumen can be a peripheral blood vessel. In some instances, inflating the inflatable body can advances the tip of the tissue penetrating element beyond external elastic lamina (EEL) of a blood vessel. In some instances, inflating the inflatable body can contact the inflatable body against inner wall of body lumen.

In some embodiments, inflating the inflatable body can comprise inflating to a first expanded configuration and then inflating to the inflatable body to a second expanded configuration larger than the first expanded configuration. In some instances, the inflatable body can comprise a first section with a first elasticity and a second section with a second elasticity such that the inflatable body is inflatable from the involuted contracted configuration to the first expanded configuration and further inflatable from the first expanded configuration to the second expanded configuration.

In some embodiments, inflating the inflatable body can change an orientation of the at least one protective element. The method can further comprise observing the orientation change of the at least one protective element to confirm inflation of the inflatable body. In some embodiments, delivering the drug to the patient can comprise providing drug through the injection port of the hub.

Another aspect of the present disclosure provides a medical instrument for localized drug delivery to tissue. The medical instrument can comprise a catheter shaft assembly having a proximal end, a distal end, a longitudinal axis between the proximal and distal ends, at least one injection lumen, at least one inflation lumen, and a guidewire lumen; a hub coupled to the proximal end of the catheter shaft assembly, the hub comprising at least one injection port coupled to the at least one injection lumen, at least one inflation port coupled to the at least one inflation lumen, and a guidewire port coupled to the guidewire lumen; an inflatable body at the distal end of the catheter shaft assembly, the inflatable body is inflatable from an involuted contracted configuration; a tissue penetrating member coupled to the inflatable body in an orientation transverse to the longitudinal axis of the catheter shaft assembly and further coupled to the injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; and a fluid routing tube coupled through the wall of the inflatable body by means of an elastomeric joint coated with parylene and connected at its proximal end to an injection lumen within the catheter shaft and connected at its distal end to the tissue penetrating member.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the medical instrument can further comprise at least one protective element coupled to inflatable body in proximity to the tissue penetrating member, at least the tip end of the tissue penetrating member being bordered by the at least one protective element when the inflatable body is in the involuted contracted configuration.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

Another aspect of the present disclosure provides a method for delivering a drug to a patient. The method can comprise providing a medical instrument according to embodiments of the present disclosure; advancing the medical instrument over a guidewire to a predetermined position within a body lumen of the patient when the inflatable body is in the involuted contracted configuration; inflating the inflatable when the catheter shaft assembly is at the predetermined position in the body lumen; and delivering the drug to the patient through the tissue penetrating member, where the tissue penetrating member is in fluid communication with a drug lumen.

In some embodiments, the injection port, the inflation port and the guidewire port can be Luer interface. The inflation port can be coupled to a pressure release valve configured to regulate a pressure of a hydraulic fluid. In some embodiments, the medical instrument can further comprise a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the medical instrument can further comprise at least one protective element coupled to inflatable body in proximity to the tissue penetrating member, at least the tip end of the tissue penetrating member being bordered by the at least one protective element when the inflatable body is in the involuted contracted configuration.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the medical instrument can further comprise a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

Another aspect of the present disclosure provides a method of manufacturing a medical instrument for localized drug delivery to tissue. The method can comprise providing a catheter shaft assembly having a proximal end, a distal end, a longitudinal axis between the proximal and distal ends, at least one injection lumen, at least one inflation lumen, and a guidewire lumen; coupling a hub to the proximal end of the catheter shaft assembly, the hub comprising at least one injection port coupled to the at least one injection lumen, at least one inflation port coupled to the at least one inflation lumen, and a guidewire port coupled to the guidewire lumen; coupling an inflatable body at the distal end of the catheter shaft assembly, the inflatable body being inflatable from an involuted contracted configuration; coupling a tissue penetrating member to the inflatable body in an orientation transverse to the longitudinal axis of the catheter shaft assembly and further to the at least one injection lumen of the catheter shaft assembly, the tissue penetrating member being coupled to the inflatable body with a tip end of the tissue penetrating member pointing outwardly of the inflatable body and enclosed within walls of the inflatable body when in the involuted contracted configuration; and coupling a fluid routing tube through the wall of the inflatable body by means of an elastomeric joint coated with parylene and connected at its proximal end to an injection lumen within the catheter shaft and connected at its distal end to the tissue penetrating member.

In some embodiments, the injection port, the inflation port and the guidewire port can be Luer interface. The inflation port can be coupled to a pressure release valve configured to regulate a pressure of a hydraulic fluid. In some embodiments, the method can further comprise attaching a labeling showing at least a parameter of the medical instrument. In some instances, the labeling can be provided at an injunction of the hub and the catheter shaft assembly. In some instances, the labeling can be provided with a color different from that of other portions of the medical instrument. In some embodiments, the catheter shaft assembly is provided with a diameter of 1 mm to 3 mm and a length of 50 cm to 180 cm. The inflatable body can be in fluid communication with the inflation lumen.

In some embodiments, the medical instrument can further comprise at least one protective element coupled to inflatable body in proximity to the tissue penetrating member, at least the tip end of the tissue penetrating member being bordered by the at least one protective element when the inflatable body is in the involuted contracted configuration.

In some embodiments, the tissue penetrating member can be in fluidic communication with a flexible drug line tubing. In some instances, the flexible drug line tubing can be routed through the wall of the inflatable body by passing through a junction of elastomeric material coated with parylene. In some instances, a proximal end of the flexible drug line tubing can be coupled to an outlet of the injection lumen of the catheter shaft assembly. The flexible drug line tubing can be made of a material which exhibiting a flexibility. For instance, the flexible drug line tubing can be made of Nitinol. In some instances, a distal end of the flexible drug line tubing can be in fluidic communication to the tissue penetrating member and is affixed to an exterior surface of the inflatable body. In some instances, the distal end of the flexible drug line tubing can be affixed to the exterior surface of the inflatable body by an adhesive. In some instances, the distal end of the flexible drug line tubing can be affixed to the exterior surface of the inflatable body by a metallic or polymer mesh-like structure, which metallic or polymer mesh-like structure being affixed to the exterior surface of the inflatable body by an adhesive. In some instances, the tissue penetrating member can be in fluidic communication with the injection lumen. In some instances, the tissue penetrating member can comprise a needle.

In some embodiments, the inflatable body can have a U-shaped cross-section in the involuted contracted configuration. At least one protective element can be provided on each lateral side of the tissue penetrating member when the inflatable body in the involuted contracted configuration. In some embodiments, the inflatable body can comprise a first section with a first elasticity and a second section with a second elasticity. In some instances, the inflatable body is inflatable from the involuted contracted configuration to a first expanded configuration and further inflatable from the first expanded configuration to a second expanded configuration larger than the first expanded configuration. The tissue penetrating member can be coupled to the second section of the inflatable body. The second elasticity can be less than the first elasticity. In some instances, the first section of the inflatable body can be made of an elastic membrane, the second section of the inflatable body can be made of an rigid polymer. In some instances, the first section can be joined edge-to-edge to the second section of the inflatable body. In some instances, the protective element can be integrated with the second section of the inflatable body.

In some embodiments, the protective element can be made of a hard polymer or a metal. For instance, the protective element can be made of platinum alloy, iridium, tungsten, or gold. The protective element can be radio-opaque. The protective element can be provided with a specific pattern or shape. In some instances, the specific pattern or shape can be asymmetric to indicate an inflation status of the inflatable body. For instance, the specific pattern or shape can comprise a triangle or arrow. In some instances, the protective element can be covered by an adhesive. In some instances, the protective element can be integrated with the inflatable body.

In some embodiments, the method can further comprise providing a torque transmission tube having an axis parallel to the axis of the catheter shaft assembly, the torque transmission tube transmitting a torque from the proximal end of the catheter shaft assembly to the distal end of the catheter shaft assembly. In some instances, the torque transmission tube can be comprised of a stainless steel hypodermic tubing that is cut in a pattern to allow a transmission of torque while removing a bending stiffness of the torque transmission tube. The torque transmission tube is coupled to one or more of the distal end of the catheter shaft assembly or the inflatable body. The torque transmission tube can be proximally fixed to a torquing element. For instance, the torquing element can be the hub. For instance, the torquing element can be a separate member at the hub.

In some embodiments, the method can further comprise coupling at least one protective element to the inflatable body in proximity to the tissue penetrating member, at least the tip end of the tissue penetrating member being bordered by the at least one protective element when the inflatable body is in the involuted contracted configuration. Inflating the inflatable body can change an orientation of the at least one protective element. The method can further comprise observing the orientation change of the at least one protective element to confirm inflation of the inflatable body.

In some embodiments, the body lumen can be a blood vessel. The body lumen can be a peripheral blood vessel. In some instances, inflating the inflatable body can advances the tip of the tissue penetrating element beyond external elastic lamina (EEL) of a blood vessel. In some instances, inflating the inflatable body can contact the inflatable body against inner wall of body lumen.

In some embodiments, inflating the inflatable body can comprise inflating to a first expanded configuration and then inflating to the inflatable body to a second expanded configuration larger than the first expanded configuration. In some instances, the inflatable body can comprise a first section with a first elasticity and a second section with a second elasticity such that the inflatable body is inflatable from the involuted contracted configuration to the first expanded configuration and further inflatable from the first expanded configuration to the second expanded configuration.

In some embodiments, inflating the inflatable body can change an orientation of the at least one protective element. The method can further comprise observing the orientation change of the at least one protective element to confirm inflation of the inflatable body. In some embodiments, delivering the drug to the patient can comprise providing drug through the injection port of the hub.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1:
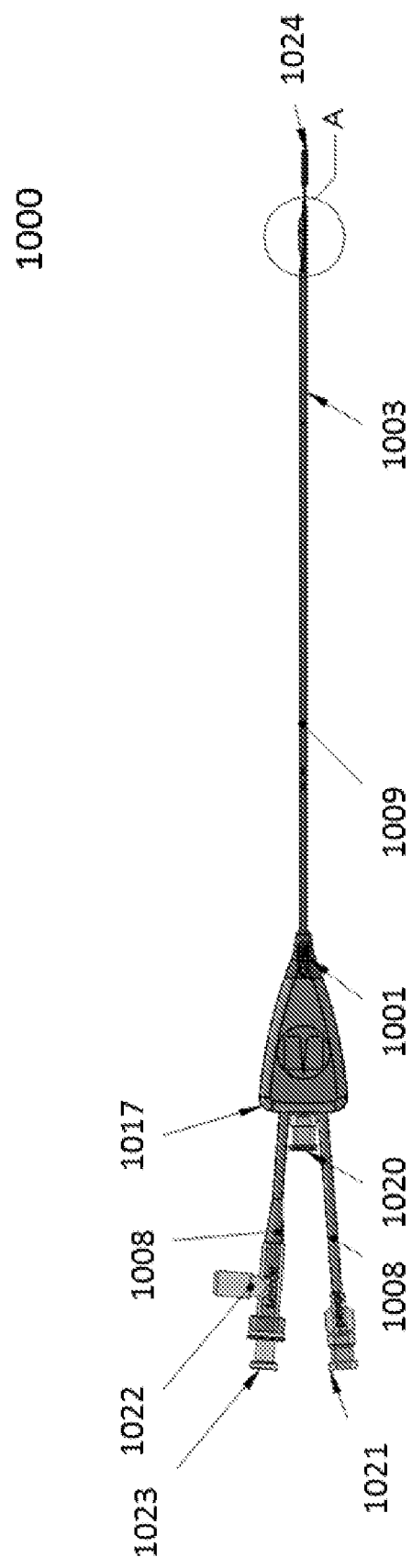
FIG. 1 is a schematic, perspective view of a medical instrument for localized drug delivery in accordance with some embodiments of the disclosure.

Reference will now be made in detail to exemplary embodiments of the disclosure, examples of which are illustrated in the accompanying drawings. Wherever possible, the same reference numbers will be used throughout the drawings and disclosure to refer to the same or like parts.

Provided herein are medical instruments and medical methods for localized drug delivery to a patient's tissue. The medical instrument can comprise a catheter shaft assembly having at least an injection lumen and an inflation lumen, an inflatable component (e.g., a balloon) at a distal end of the catheter shaft assembly and in fluid communication to the inflation lumen, a tissue penetrating member (e.g., a needle) coupled to the inflatable component and in fluid communication to the injection lumen, fluid routing pathways between the catheter shaft assembly and the inflatable component and between the catheter shaft assembly and the tissue penetrating member, and at least one protective element coupled to the inflatable component in proximity to the tissue penetrating member. The catheter shaft assembly can be inserted into and advanced within a body lumen of a patient over a guidewire to a predetermined position within the body lumen when the inflatable component is in a contracted configuration. The inflatable component can then be inflated by hydraulic fluid, which is supplied through the inflation lumen, into an expanded configuration such that the tissue penetrating member is exposed. The tissue penetrating member, which is in fluidic communication with a drug lumen, can penetrate the body lumen and deliver a drug into the patient's tissue. The inflatable component can be deflated upon a completion of the drug delivery, such that the catheter shaft assembly can be further advanced in or retracted from the body lumen. The inflatable component and a fluid communication line from the injection lumen to the tissue penetrating element can be kept separate and sealed off from each other using fluid routing techniques between the catheter shaft assembly and the inflatable component. The body lumen can comprise at least one of a blood vessel or a peripheral blood vessel of a patient.

The at least one protective element can be configured to protect the inflatable component from a damage caused by the tissue penetrating member. For example, the protective element can protect the flexible inflatable component during a placement of the catheter shaft assembly and an inflation of the inflatable component. The protective element can be further configured to provide an indication on the position of the tissue penetrating member and/or an inflation status of the inflatable component. In some instances, the protective element can be radio-opaque to provide feedback on X-ray imaging of the catheter shaft assembly. The protective element can also be provided with a specific pattern/shape, for example a triangle, a letter or a number, to indicate an inflation status of the inflatable component.

FIG. 1 is a schematic, perspective view of a medical instrument 1000 for localized drug delivery in accordance with some embodiments of the disclosure. The medical instrument 1000 can comprise a catheter shaft assembly 1009 and a hub 1017 coupled to a proximal end of the catheter shaft assembly 1009. A labeling 1001 can be provided to the medical instrument to show particular information for the medical instrument, such as the working diameter of patient body lumens that the medical instrument can treat. The labeling 1001 can be provided at any appropriate position of the medical instrument, for example at the hub or at an injunction of the hub and the catheter shaft assembly. In some instances, the labeling can be provided with a color different from that of other portions of the medical instrument.

The catheter shaft assembly 1009 can be provided as a micro-fabricated intraluminal catheter. The catheter shaft assembly can include a catheter body tubing. In some embodiments, the catheter body tubing can be provided with a diameter of 1 mm to 3 mm and a length of 50 cm to 180 cm. One or more lumens (e.g., fluid transmission channels) can be accommodated within the catheter body tubing, which one or more lumens each has a longitudinal axis parallel to a longitudinal axis of the catheter body tubing. The one or more lumens can include at least one of an injection lumen, in inflation lumen, or a guidewire lumen. The injection lumen can be provided to transmit a drug or agent to be delivered to the patient. The inflation lumen can be provided to transmit a fluid to inflate an inflatable component (e.g., a balloon). The guidewire lumen can be provided through which a guidewire can be extended. In some embodiments where a guidewire lumen is not provided within the catheter shaft assembly, a stiffening element 1024 can be provided at the distal end of the catheter shaft assembly.

In some embodiments, the catheter shaft assembly can additionally include a torque transmission tube 1003 with its axis parallel to the axis of the catheter body tubing. The torque transmission tube can be provided to transmit a torque from the proximal end (e.g., the user end) of the catheter shaft assembly to the distal end (e.g., the working end) of the catheter shaft assembly. The torque transmission tube may be comprised of a stainless steel hypodermic tubing that is cut in a pattern to allow the transmission of torque while removing the bending stiffness of the tube. An exemplary cut pattern is a spiral cut or a broken spiral cut as described in U.S. Pat. No. 7,708,704, the full disclosures of which is incorporated herein by reference. The torque transmission tube can be distally fixed or bonded to the catheter shaft assembly or the inflatable component or both. The torque transmission tube can be proximally bonded to a torquing element at the proximal end of the medical instrument, which may be the hub or a separate piece from the hub, oriented distal or proximal to the hub. By locating the torquing element separate from the hub, the distal end of the medical instrument may be twisted, or torqued, without twisting the hub. The torquing element may have access ports which are cut into the torquing element to allow for bonding of distal elements such as fluid channels. Access ports may be cut through the torquing element and a multi-lumen catheter tubing to provide access for bonding a tubing into one of the lumens of the catheter shaft by way of adhesive injection through the access port.

The hub 1017 can be coupled to the proximal end of the catheter shaft assembly 1009 and comprise one or more interfaces/ports which are in fluidic communication with the one or more lumens of the catheter body tubing. The one or more interfaces/ports can be coupled to the one or more lumens of the catheter body tubing via a tube such as tube 1008. In some embodiments, the hub can comprise an injection port 1021 coupled to the injection lumen, an inflation port 1023 coupled to the inflation lumen, and a guidewire port 1020 coupled to the guidewire lumen of the catheter body tubing. In an example where the medical instrument has a scope-compatible configuration, the injection port 1021 and the inflation port 1023 can be provided. In another example, where the medical instrument has a guidewire-compatible configuration, the guidewire port 1020 can be additionally provided. The one or more tubes can be coupled with the catheter body tubing by adhesive bonding, potting, thermal fusing, or over-molding, for example. The one or more interfaces/ports of the hub can be Luer interfaces or handles with which a user can interact with the medical instrument to provide or remove a hydraulic fluid, guidewire and drug(s) into or from the medical instrument. For instance, the hydraulic fluid can be supplied inti the inflatable component via the inflation lumen using a syringe. In some embodiments, the one or more interfaces/ports of the hub can each be provided with a pressure governor to regulate a pressure of the fluid transmitted via the interface/port. For instance, a pressure governor 1022 can be provided to the inflation port 1023. The pressure governor 1022 can be a pressure relief valve with spring loaded silicone stopper against a valve seat. The pressure governor 1022 can be configured to regulate a pressure of the hydraulic fluid supplied to the inflatable component.

Figure 2:
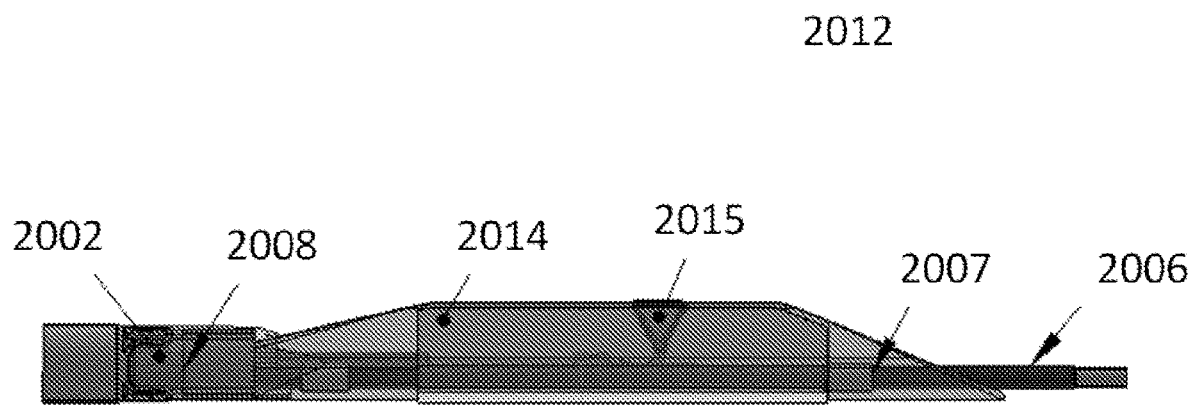
FIG. 2 is an enlarged view showing portion A of FIG. 1.

The inflatable component can be provided at a distal end of the catheter shaft assembly. FIG. 2 is an enlarged view showing portion A of FIG. 1 where the inflatable component is positioned. In some embodiments, the inflatable component can comprise an inflatable body 2012 and a protective element 2015 provided at the inflatable body 2012. The inflatable body 2012 can be coupled to the inflation lumen by various coupling member, such as an adhesive 2007. The protective element 2015 can be provided to prevent any damage of the inflatable body during an inflation process, and will be described hereinafter.

The inflatable body 2012 can be a hydraulic actuating balloon which is inflatable when a hydraulic fluid is provided into the hydraulic actuating balloon. For instance, the hydraulic actuating balloon can be made from an elastic material. The hydraulic fluid can be a compressed air or liquid. In some embodiments, the inflatable body 2012 can include a first section and a second section which are inflated and deployed sequentially and/or successively. For instance, the first section of the inflatable body can be inflated and/or deployed at a first pressure, and the second section of the inflatable body can then be inflated and/or deployed at a second pressure which is higher than the first pressure. The second section may not be inflated during an inflation of the first section. The first section may not be further inflated during an inflation of the second section. In some instances, the first pressure and the second pressure can be successive inflation pressures. The sequential inflation can be effected by providing the first section and the second section with different elasticities. The sections of differing elasticity in the inflation portion can be achieved and fabricated in a variety of ways. In an exemplary embodiment, the sections are formed in an edge-to-edge manner or along an overlapping border region using an appropriate masking and deposition technique. It will be appreciated that, the sections can also be formed by layering materials of differing elasticities, providing layers having different thicknesses, providing reinforcement fibers or materials which create sections of different elasticity within a matrix of the same material, providing tethers and other stretchable or breakable elements within sections of the inflation portion which yield or break when pressures are applied above threshold levels, and the like. It will be appreciated that, multiple first sections and/or multiple second sections can be provided, such that an inflation/actuation of the inflation portion can be customized. Similar inflatable bodies with multiple layers and methods for manufacturing such layers are described in U.S. patent application Ser. No. 11/858,797 (U.S. Pat. No. 7,691, 080), Ser. No. 12/711,141 (U.S. Pat. No. 8,016,786), Ser. No. 13/222,977 (U.S. Pat. No. 8,721,590), Ser. No. 14/063, 604 (U.S. Pat. No. 9,789,276), and Ser. No. 15/691,138, the contents of which are fully incorporated herein by reference.

A material of the inflatable body 2012 can allow the inflatable body to be inflated/converted from a lower profile to a larger profile once an inflation pressure is applied to the inflatable body, such that a size of the inflatable body can be increased. The inflatable body can be made of a thin, semi-flexible but relatively non-distensible material, such as a polymer, for instance, Parylene (types C, D, F or N), silicone, polyurethane, Nylon, Pebax or polyimide. The inflatable body can return substantially to its original configuration and orientation (e.g., the unactuated/uninflated condition) when the hydraulic fluid is removed. The inflatable body can be capable of withstanding pressures of up to about 300 psi upon application of the hydraulic fluid.

Figure 3A:
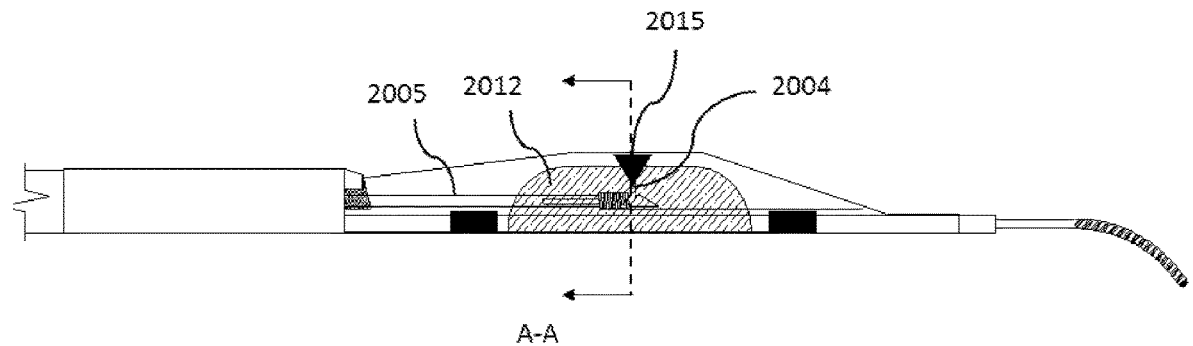
FIG. 3A shows the medical instrument for localized drug delivery where a tissue penetrating member is not yet deployed in accordance with some embodiments of the disclosure.

As shown in FIG. 3A, at least one tissue penetrating member 2004 can be coupled to the inflatable body 2012 in an orientation transverse to the longitudinal axis of the catheter shaft assembly 1009. The tissue penetrating member 2004 can be a needle which is configured to penetrate into a luminal wall and/or deliver a drug into the luminal wall. The tissue penetrating member 2004 can be another structure such as an atherectomy blade, an optical fiber for delivering laser energy, a mechanical abrasion, or a drilling component, to name a few examples. In some embodiments, the tissue penetrating member can comprise at least one needle or microneedle.

The tissue penetrating member can be in fluidic communication with a flexible drug line tubing 2005. The flexible drug line tubing 2005 can be a separate tubing piece which is received in the injection lumen of the catheter shaft assembly 1009 and in fluidic communication with the injection port at the hub, such that a pharmaceutical agent or a diagnostic agent can be transmitted from the injection port 1021 to the tissue penetrating member along the flexible drug line tubing 2005. Alternatively or in combination, a proximal end of the flexible drug line tubing 2005 can be coupled to an outlet of the injection lumen of the catheter shaft assembly 1009. The flexible drug line tubing 2005 can be made of an appropriate material which exhibits a flexibility or shape memory property. In some instances, the flexible drug line tubing can be made from Nitinol. In other instances, the flexible drug line tubing can be made from polyimide, PEEK, Pebax, or other stiff medical polymers. A distal end of the flexible drug line tubing 2005 proximal to the location that the tissue penetrating member bends upright can be in fluidic communication to the tissue penetrating member and can be affixed to an exterior surface of the inflatable body 2012. The distal end of the flexible drug line tubing can be affixed to the exterior surface of the inflatable body 2012 by an adhesive, such as cyanoacrylate. Alternatively or in combination, the distal end of the flexible drug line tubing can be joined to the exterior surface of the inflatable body by a metallic or polymer mesh-like structure, which is itself affixed to the exterior surface of the inflatable body by an adhesive. The mesh-like structure may be made of, for instance, steel or nylon. Alternatively or in combination, the distal end of the flexible drug line tubing can be joined to the exterior surface of the inflatable body by an integrated tube or tunnel affixed or adhered to the wall of the inflatable body by an adhesive such as cyanoacrylate, light-cure adhesive, silicone adhesive, or by vapor coatings such as parylene.

In some instances, the flexible drug line tubing can be routed through the wall of the inflatable body by passing through a junction of elastomeric material coated with parylene. The flexible drug line tubing can be provided within the inflatable body and routed through the inflatable body at the distal end of the flexible drug line tubing. A junction of elastomeric material coated with parylene can be provided at the inflatable body where the flexible drug line tubing passes from the interior of the inflatable body to the exterior of the inflatable body, such that the flexible drug line tubing is sealed against the inflatable body at the junction.

Figure 3B:
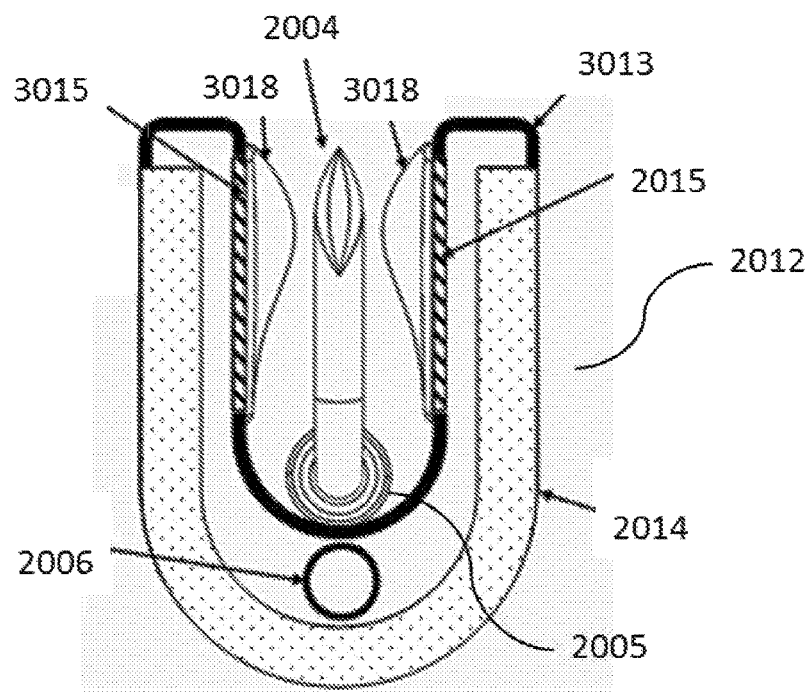
FIG. 3B is a cross-sectional view along line A-A of FIG. 3A.

The medical instrument shown in FIG. 3A has an involuted contracted configuration where the tissue penetrating member (e.g., a needle) is not deployed/exposed. The catheter shaft assembly, in use, can be inserted in and advanced along the patient's body lumen in this involuted contracted configuration until it reaches a target region within the body lumen. FIG. 3B is a cross-sectional view along line A-A of FIG. 3A. As shown in FIG. 3B, the inflatable body 2012 can include a first section 3013 and a second section 2014. In some embodiments, the first section 3013 can be an elastic membrane having a first elasticity, and the second section 2014 can be a rigid polymer (e.g., parylene) having a second elasticity which is less than the first elasticity, such that the first section and the second section can be successively inflated. Here, the parameter elasticity means the ability of a body to resist a distorting influence and to return to its original size and shape when that influence or force is removed. An object having a smaller elasticity can be more rigid and can be inflated under greater pressure. Alternatively, the object having smaller elasticity may be more stretchy than the object with greater elasticity, but the object with greater elasticity (e.g., the first section 3013) may undergo bending stress to open the expandable member from the involuted configuration without further stretching, while the object with less elasticity (e.g., the second section 2014) may secondarily stretch after the expandable cavity has formed a roughly circular cross-sectional shape, thus expanding the pressurized component's diameter as pressure is increased.

In the involuted contracted configuration shown in FIGS. 3A and 3B, the inflatable body 2012 can have a substantially U-shaped cross-section. The tissue penetrating member 2004 such as a needle can be coupled to the first section 3013 of the inflatable body 2012 in an orientation transverse to the longitudinal axis of the catheter shaft assembly. The tissue penetrating member 2004 can be further coupled to the injection lumen of the catheter shaft assembly via the flexible drug line tubing 2005. In the involuted contracted configuration, the needle can be coupled to the second section of the inflatable component with the needle tip pointing outwardly of the inflatable component and enclosed within walls of the inflatable component. As shown in FIG. 3B, the needle can extend approximately perpendicularly from the exterior surface of the second section of the inflatable body. Therefore, once actuated, the needle can move substantially perpendicularly to the longitudinal axis of the catheter shaft assembly and/or the injection lumen into which the flexible drug line tubing is coupled, to allow direct puncture or breach of body lumen walls.

The needle can include the sharp needle tip and a needle shaft. The needle tip can provide an insertion edge or point.

The needle shaft can be hollow and in fluidic communication with the distal end of the flexible drug line tubing. The needle tip can have an outlet port, permitting an injection of a pharmaceutical or drug into the patient. The needle, however, may not need to be hollow, as it may be configured like a neural probe or electrode to accomplish other tasks. The needle can be a 27-gauge, or smaller, steel needle. The needle can have a penetration length of between 0.4 mm and 4 mm. Alternatively or in combination, the microneedle can be microfabricated from polymers, other metals, metal alloys or semiconductor materials. The needle, for example, can be made of stainless steel, Nitinol, Parylene, silicon or glass.

At least one protective element 2015 can be coupled to the second section of the inflatable body 2012 at a position in proximity to the tissue penetrating member (e.g., a needle). The least one protective element 2015 can be configured such that at least the tip end of the needle can be bordered by the at least one protective element 2015 at least when the inflatable body is in the involuted contracted configuration. As shown in the cross-sectional view of FIG. 3B, at least one protective element 2015 can be provided at each lateral side of the needle, such that the needle is sheathed and protected by the protective element when the inflatable body is in the involuted contracted configuration. For instance, the protective element can be placed to surround to the sharp needle tip and function to protect the inflatable body from needle tip penetration or damage during transit of the medical instrument into and out of the body lumen.

The protective element 2015 can be integrated into an exterior wall of the second section of the inflatable body 2012. The protective element can be encapsulated by, for example parylene, and can additionally be covered by a soft adhesive 3018 such as silicone, as shown in the cross-sectional view of FIG. 3B. In some embodiments, the protective elements can be built directly into the exterior wall of the inflatable body 2012 by coating them with silicone adhesive, adhering them to a dissolvable substrate, coating the substrate with parylene, and dissolving the substrate. In this way, the protective elements and surrounding silicone can be integrated with the parylene coating and remain permanently intact to the exterior wall of the inflatable body.

The protective elements can be comprised of a hard polymer or metal. The protective elements can be made of, for example, stainless steel, platinum alloy, iridium, tungsten, gold, or the like. The protective elements can be radio-opaque to provide feedback on X-ray imaging of the catheter shaft assembly. The protective elements can be provided with a specific pattern/shape to provide an indication on an inflation status of the inflatable body. The specific pattern/shape can be any suitable shape, symbol, number or letter that can display different patterns/shapes under different configurations of the protective elements. In some embodiments, the specific pattern/shape can be asymmetric such as a triangle or an arrow. For instance, as shown in FIG. 3A, the protective elements can be provided to have an isosceles triangle shape with the vertex pointing downwards when the inflatable body is in the involuted contracted configuration. With the aid of X-ray imaging, an operator of the medical instrument can determine that the inflatable body is in the involuted contracted configuration and/or another specific configuration (e.g., a partially inflated configuration, as will be discussed below) when the protective elements is in the specific shape of an isosceles triangle shape with the vertex pointing downwards. The operator of the medical instrument can otherwise determine that the inflatable body is in a different configuration when the shape of the protective elements is changed (e.g., a fully inflated configuration), as will be discussed below.

Figure 4A:
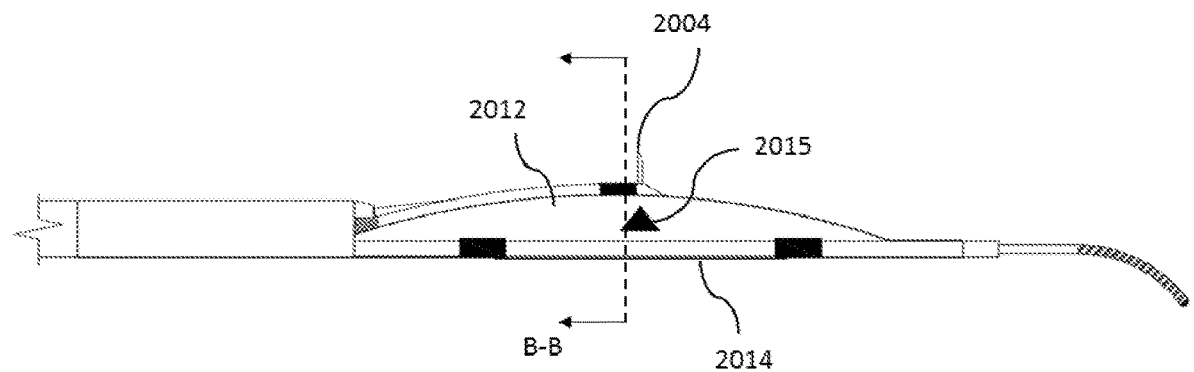
FIG. 4A shows the medical instrument for localized drug delivery where an inflatable body is at a partially inflated configuration in accordance with some embodiments of the disclosure.
Figure 4B:
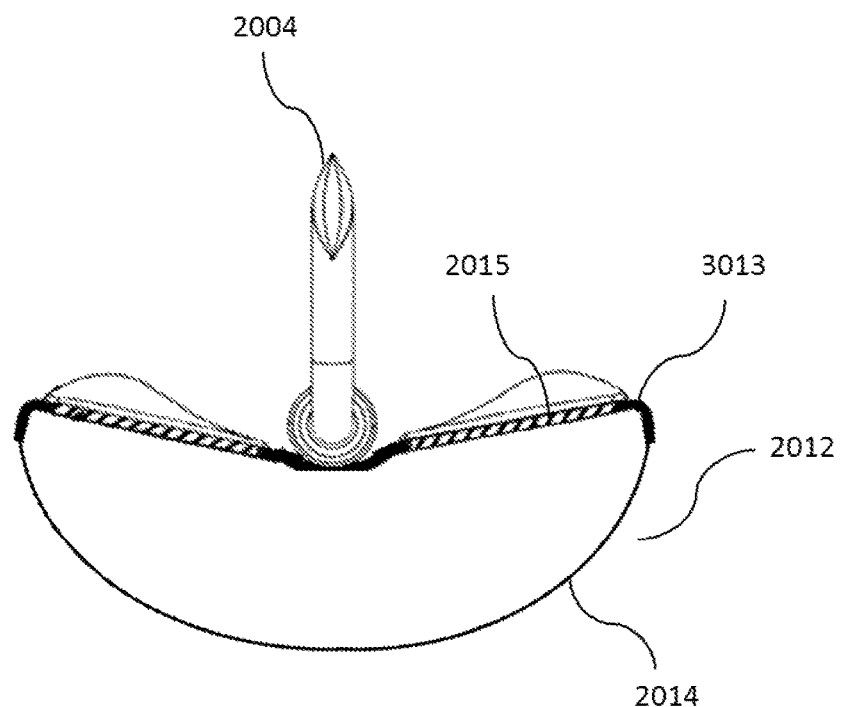
FIG. 4B is a cross-sectional view along line B-B of FIG. 4A, showing a transitional configuration toward the partially inflated configuration of inflatable body.
Figure 4C:
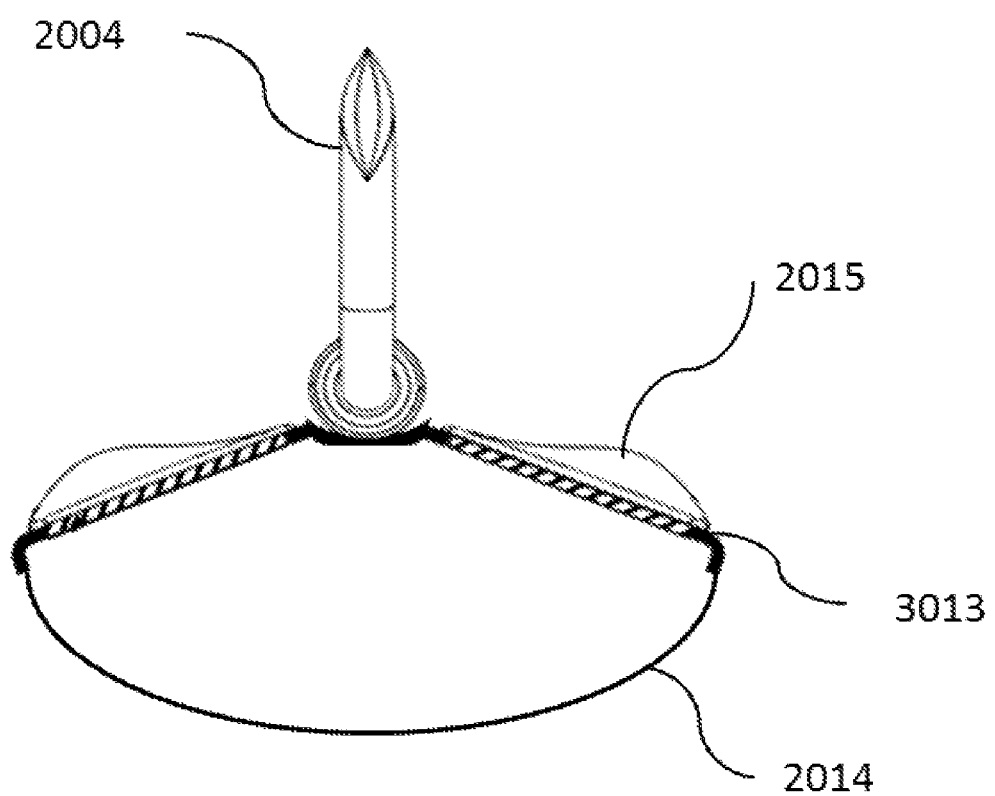
FIG. 4C is a cross-sectional view along line B-B of FIG. 4A, showing the partially inflated configuration of inflatable body.
Figure 5A:
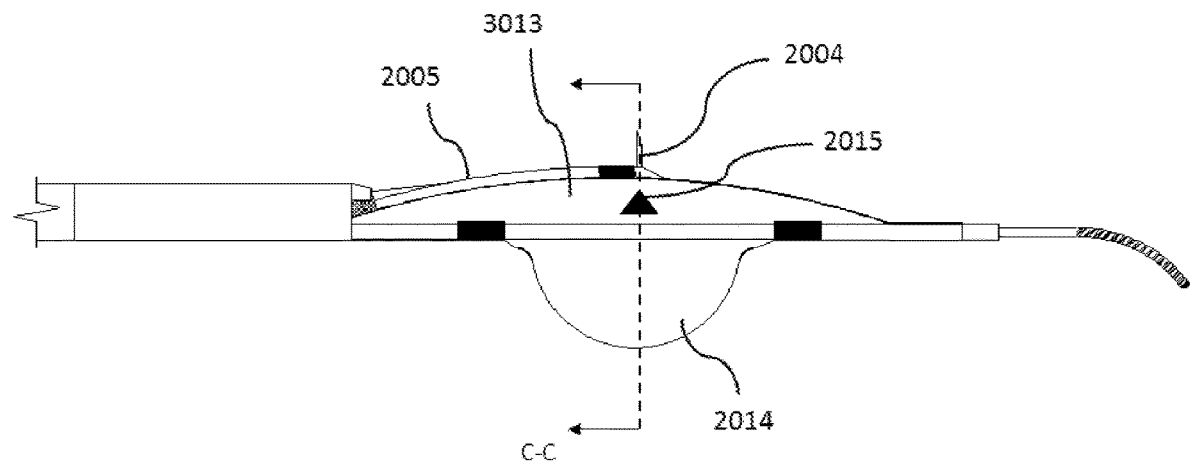
FIG. 5A shows the medical instrument for localized drug delivery where the inflatable body is at a fully inflated configuration and the tissue penetrating member is deployed in accordance with some embodiments of the disclosure.
Figure 5B:
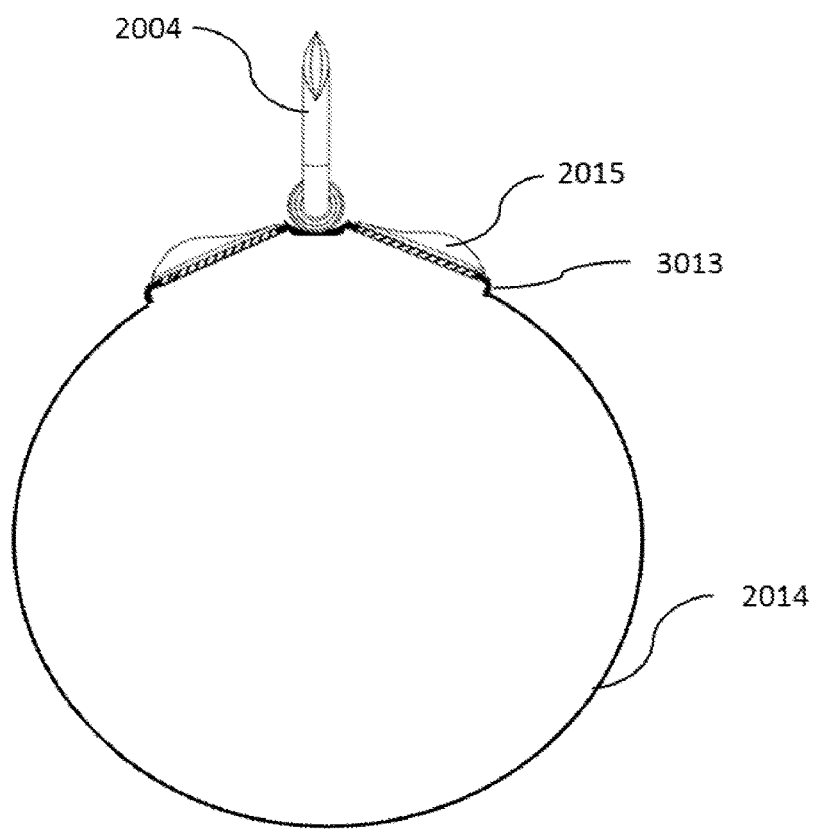
FIG. 5B is a cross-sectional view along line C-C of FIG. 5A.

FIG. 4A shows the medical instrument for localized drug delivery where an inflatable body is at a partially inflated configuration. FIG. 4B is a cross-sectional view along line B-B of FIG. 4A, showing a transitional configuration toward the partially inflated configuration of inflatable body. FIG. 4C is a cross-sectional view along line B-B of FIG. 4A, showing a partially inflated configuration of inflatable body. FIG. 5A shows the medical instrument for localized drug delivery where the inflatable body is at a fully inflated configuration and the tissue penetrating member is deployed. FIG. 5B is a cross-sectional view along line C-C of FIG. 5A.

The inflatable body 2012 shown in FIGS. 4A and 4C has a first expanded configuration where the inflatable body is partially inflated by the hydraulic pressure which is built up in the inflatable body. The hydraulic pressure can be generated by the inflation/hydraulic fluid which is supplied into the inflatable body through the inflation lumen. In some embodiments, the first section 3013 of the inflatable body 2012 can be a hinge-like structure that unbends and inverts at a lower activation pressure, leading to a round cross section of the inflated device at a lower activation pressure, as shown in FIG. 4C. Then as activation pressure is increased, the second section 2014 stretches to expand the size of the inflatable body 2012, as shown in FIG. 5B. In other words, the first section 3013 of the inflatable body 2012 can be inflated prior to an inflation of the second section 2014 which is composed of an elastomeric membrane component. The pressure at which the first section 3013 unfolds may be, for example, between 1 and 20 psi, while the pressure at which the second section 2014 stretches may be, for example, in the range from 5 to 200 psi. In an exemplary embodiment, the first section 3013 may completely unfold at 5 to 10 psi, leading to a total diameter of the inflatable body 2012 of 3 millimeters, for example, while expansion of the second section 2014 is minimal prior to addition of 10 psi, but increases sharply from 10 psi to 40 psi and leads to growth of the diameter from 3 to 6 mm.

As shown in FIG. 4C, in the first expanded configuration, the first section 3013 of the inflatable body 2012 has reached its rounded shape while the second section 2014 does not start to inflate or stretch. The tissue penetrating member 2004 can be sheathed and protected by the protective element during the inflatable body transitioning from the configuration shown in FIG. 3B to the transitional configuration shown in FIG. 4B and then the first expanded configuration shown in FIG. 4C. A pattern/shape of the protective elements 2015 in the first expanded configuration can change with respect to the pattern/shape of the protective elements in the involuted contracted configuration. For instance, the protective elements can invert directionally such that the isosceles triangle shape has a vertex pointing downwards when the inflatable body is in the first expanded configuration and pointing upwards with the inflatable body is in the second expanded configuration.

The inflatable body 2012 shown in FIGS. 5A and 5B has a second expanded configuration where the inflatable body is fully inflated by the increased hydraulic pressure in the inflatable body. The inflatable body 2012 in the second expanded configuration can have a larger profile than the first expanded configuration as both the first section 3013 and the second section 2014 of the inflatable body 2012 have reached their rounded shape. A coupling between the tissue penetrating member 2004 and the exterior surface of the first section 3013 of the inflatable body 2012 can be maintained due to a flexibility of the flexible drug line tubing 2005. In other words, the flexible drug line tubing 2005 can be deformed to conform to the expanded exterior surface of the first section 3013. The tissue penetrating member 2004 can remain in fluidic communication with the injection lumen of the catheter shaft assembly via the flexible drug line tubing 2005 in this second expanded configuration, such that a therapeutic or diagnostic agent can be delivered to the target region of the patient through the tissue penetrating member.

Figure 6A:
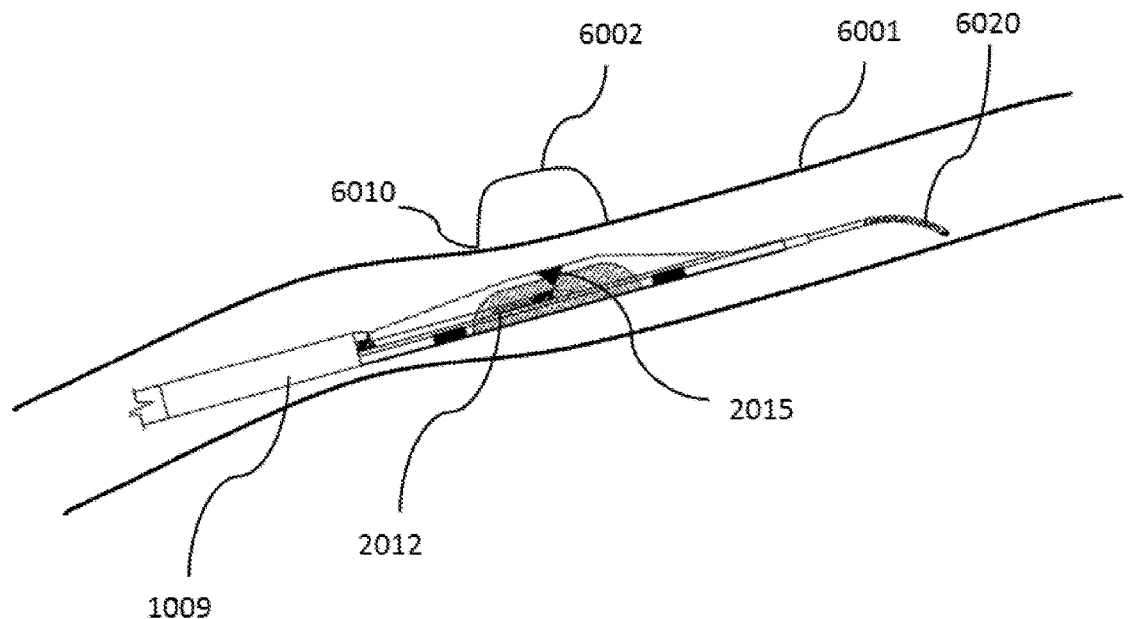
FIG. 6A is a schematic, perspective view of the medical instrument for localized drug delivery as being inserted into a patient's body lumen in accordance with some embodiments of the disclosure.

FIG. 6A shows the medical instrument for localized drug delivery as being inserted into a patient's body lumen. The catheter shaft assembly 1009 of the medical instrument can be inserted through an opening in the body (e.g., for bronchial or sinus treatment) or through a percutaneous puncture site (e.g., for artery or venous treatment) of the patient and moved within the patient's body lumen 6001, until a target region 6010 is reached. The catheter shaft assembly can be inserted and moved in the body lumen in the involuted contracted configuration where the inflatable body has a minimum profile and the tissue penetrating member (e.g., needle) is not deployed.

The target region 6010 can be a region where the body lumen tissue 6002 is positioned, and the body lumen tissue 6002 can be the tissue to which the therapeutic or diagnostic agents are to be delivered. The target region 6010 can be the site of tissue damage or more usually can be adjacent the sites typically being within 100 mm or less to allow migration of the therapeutic or diagnostic agent. The catheter shaft assembly can follow a guide wire 6020 that has previously been inserted into the patient. Optionally, the catheter shaft assembly can also follow the path of a previously-inserted guide catheter (not shown) that encompasses the guide wire.

As the catheter shaft assembly is guided inside the patient's body, the inflatable body 2012 can remain deflated and the needle can be held inside the U-shaped inflatable body, such that no trauma is caused to the body lumen walls. During maneuvering of the catheter shaft assembly, an imaging technique can be used to image the catheter shaft assembly and assist in positioning the inflatable body and the tissue penetrating member at the target region. The imaging technique can include at least one of a fluoroscopy, X-ray, or magnetic resonance imaging (MRI). For instance, the protective elements 2015 can be radio-opaque to provide feedback on X-ray imaging of the tissue penetrating member and/or the inflatable body. The protective elements 2015 can be provided with a specific pattern/shape such as an isosceles triangle shape with the vertex pointing downwards. For instance, the operator of the medical instrument can determine from this specific isosceles triangle shape with the vertex pointing downwards on the X-ray imaging that the inflatable body is not fully inflated (e.g., in the involuted contracted configuration or the first expanded configuration).

Figure 6B:
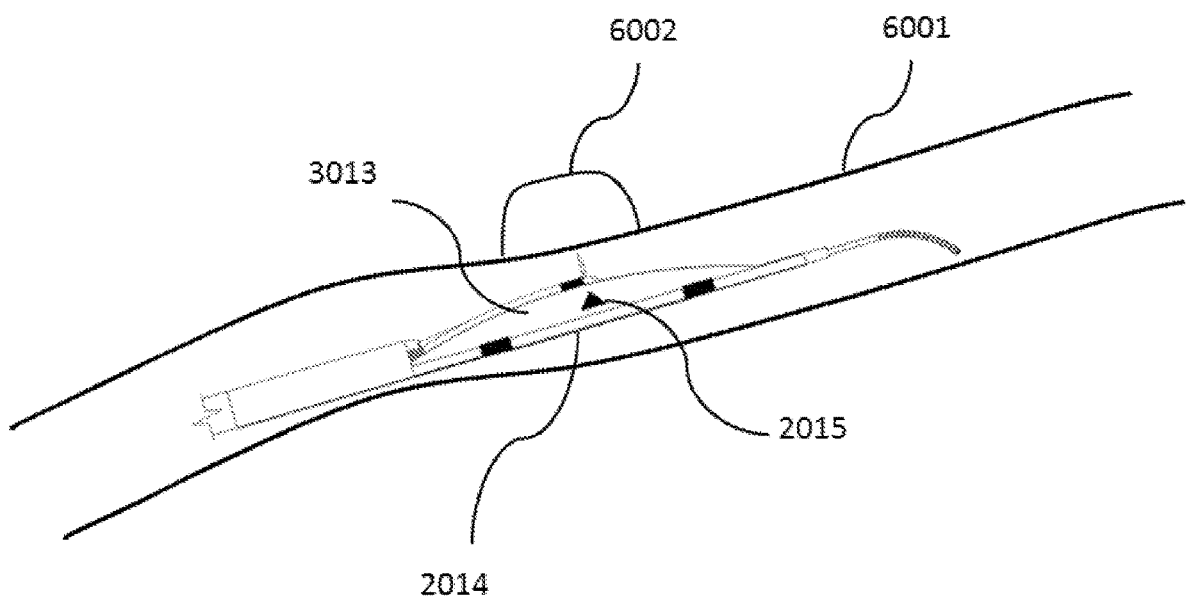
FIG. 6B is a schematic, perspective view of the medical instrument for localized drug delivery as the tissue penetrating member is deployed in the patient's body lumen in accordance with some embodiments of the disclosure.

FIG. 6B shows the medical instrument for localized drug delivery as the inflatable component being partially inflated in the patient's body lumen. After being positioned at the target region, a movement of the catheter shaft assembly can be terminated and the hydraulic fluid can be supplied into the inflatable body, causing the inflatable body to inflate into the first expanded configuration where the first section 3013 of the inflatable body is inflate/expand while the second section 2014 of the inflatable body maintains deflated. As shown, in the first expanded configuration, the first section 3013 of the inflatable body 2012 has reached its rounded shape while the second section 2014 does not start to meaningfully inflate or stretch. The inflated first section 3013 can touch the lumen wall which is opposite to the body lumen tissue 6002, and raise/move the inflatable body towards the body lumen tissue 6002. The second section of the inflatable body 2014 may not be expanded in the first expanded configuration. This is particularly useful in smaller vessels where the second section 2014 of the inflatable body 2012 is not required to expand in order to penetrate the tissue penetrating element through the vessel wall. In larger vessels, additional pressure may cause the second section 2014 of the inflatable body 2012 to stretch and the inflatable body 2012 may reach a larger diameter to seat the penetrating element into and through the vessel wall.

Figure 6C:
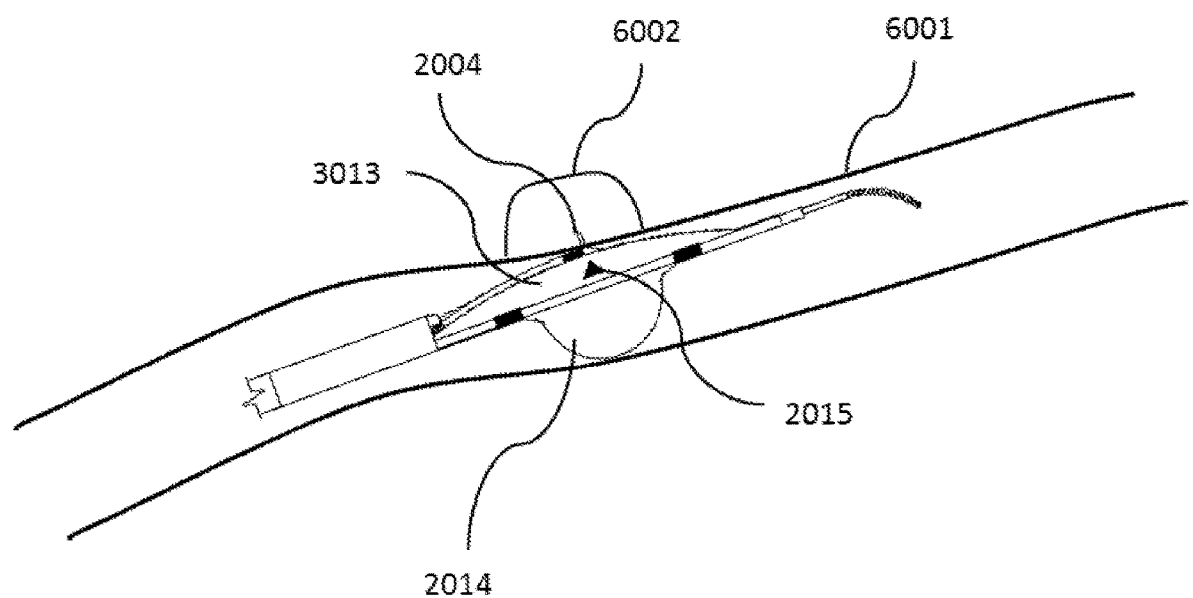
FIG. 6C is a schematic, perspective view of the medical instrument for localized drug delivery as the tissue penetrating member penetrating into a luminal wall of the patient's body lumen in accordance with some embodiments of the disclosure.

FIG. 6C shows the medical instrument for localized drug delivery as the inflatable body being fully inflated and the tissue penetrating member being deployed to penetrate into a luminal wall. The inflatable body can be converted into the second expanded configuration from the first expanded configuration as the hydraulic pressure in the inflatable body increases as a result of a continuous supplement of the hydraulic fluid from the inflation lumen. In the second expanded configuration, the inflatable body can be fully inflated where both the first section 3013 and the second section 2014 of the inflatable body reach their fully expanded shape. The inversion of the first section 3013 of the inflatable body can move the tissue penetrating member 2004 in a direction substantially perpendicular to the axis of the catheter shaft assembly to puncture the wall of the body lumen 6001 and advance into the body lumen tissue 6002 as well as the adventitia, media, or intima surrounding body lumens. For instance, the tissue penetrating member can be moved by the second section of the inflatable body beyond an external elastic lamina (EEL) of a blood vessel. The inflated second section 3013 of the inflatable body can allow contacting/abutting against the lumen wall which is opposite to the body lumen tissue 6002 during the tissue penetrating member puncturing into the body lumen tissue, such that a penetration depth of the tissue penetrating member can be maximized as a result of a supporting from the inflated first section.

In an exemplary embodiment, the catheter shaft assembly can be positioned in a peripheral blood vessel. The tissue penetrating member can be advance into a luminal tissue. The therapeutic or diagnostic agents may then be introduced through the flexible drug line tubing in order to introduce a plume of agent in the cardiac tissue. The plume can be within or adjacent to the region of tissue damage. The progressive inflation of the inflatable body provides optimal apposition of the needle through the vessel wall regardless of diameter. Thus, a variable diameter system is created in which the same catheter may be employed in lumens throughout the body that are within a range of diameters. The needle can be injected into tissue fully up to its point of attachment to the inflatable body, thus maximizing the needle penetration depth.

As shown in FIG. 6C, a pattern/shape of the protective elements 2015 can be changed with respect to that shown in FIG. 6A and FIG. 6B. The operator of the medical instrument can determine from this change in the pattern/shape of the protective elements that an inflation status of the inflatable body and/or a development status of the tissue penetrating member have been changed. For instance, the specific isosceles triangle shape with the vertex pointing downwards can be changed to an isosceles triangle shape with the vertex pointing upwards when the first section of the inflatable body is inverted from the involuted configuration to the first expanded configuration. This change in the pattern/shape of the protective elements on X-ray imaging of the inflatable component can function as an indicator that the tissue penetrating member has been fully deployed.

After actuation of the tissue penetrating member (e.g., needle) and delivery of the drugs/agents to the target region through the tissue penetrating member, the hydraulic fluid can be exhausted from the inflatable body, causing the inflatable body to return to its original, involuted contracted state. The tissue penetrating member, being withdrawn, can once again be sheathed by the protective element. Once the inflatable body is deflated and the tissue penetrating member is withdrawn, the catheter shaft assembly can either be repositioned for further drug delivery or withdrawn from the patient's body lumen.

Typical dimensions for the body lumens are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1.5 mm. The hydraulic pressure useful to cause actuation of the inflatable body is typically in the range from 0.1 atmospheres to 20 atmospheres, more typically in the range from 0.5 to 20 atmospheres, and often in the range from 1 to 10 atmospheres. It may take only between approximately 100 milliseconds and five seconds for the tissue penetrating member to move from its furled state to its unfurled state.

Various microfabricated devices can be integrated into the tissue penetrating member and/or the inflatable body for metering flows, capturing samples of biological tissue, and measuring pH. For instance, electrical sensors for measuring the flow through the tissue penetrating member as well as the pH of the pharmaceutical being deployed can be provided to the tissue penetrating member. For such complete systems, high integrity electrical, mechanical and fluid connections are provided to transfer power, energy, and pharmaceuticals or biological agents with reliability.

The fluid routing pathways can remain distinct for the elements of the catheter: a path for guidewire, a path for inflation fluid or medium, and a path for drug delivery through the tissue penetrating element. At the distal end of the catheter, these pathways can be difficult to seal off from each other, and leaks or cross-talk can occur. Therefore, there is a need to distinguish the fluid pathways from each other.

Figure 7A:
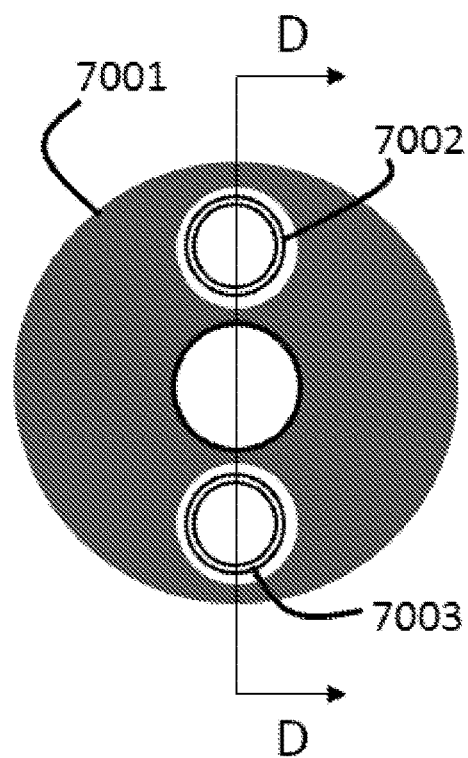
FIG. 7A is a cross-sectional view of the junction between three-lumen catheter tubing and the three fluid paths created by use of elastomeric coating and vapor polymer deposition, in accordance with some embodiments of the disclosure.
Figure 7B:
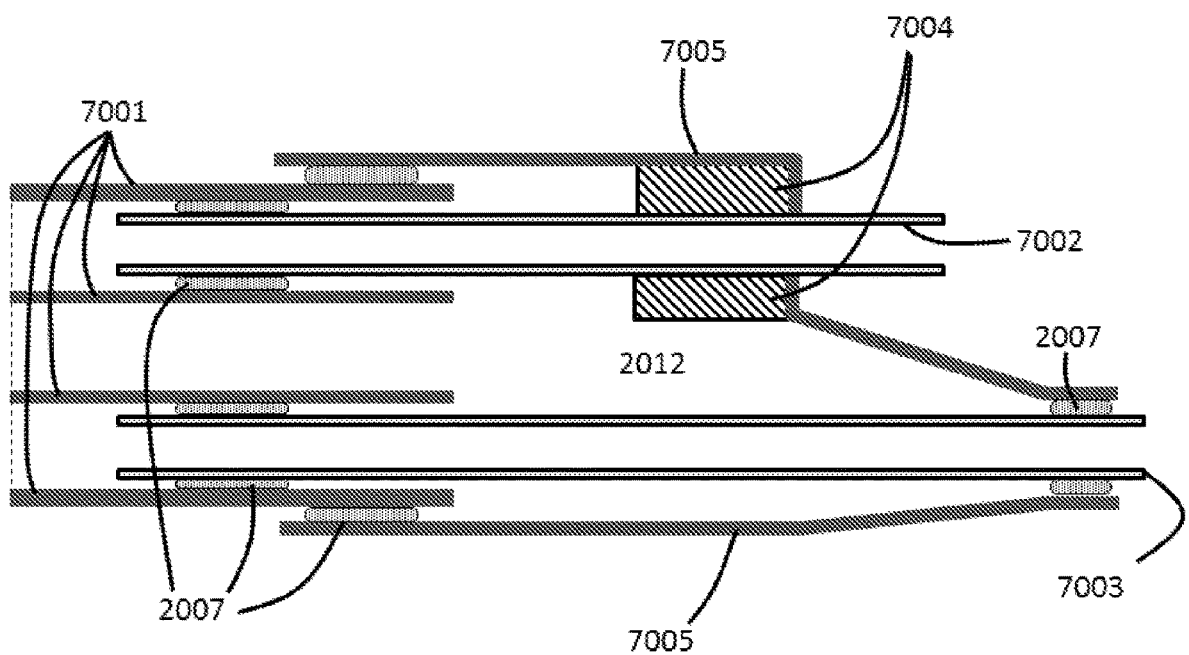
FIG. 7B is a cross-sectional view along line D-D of FIG. 7A.

FIG. 7A shows an embodiment useful for routing fluids from a multi-lumen catheter tubing 7001 into separate tubes 7002 and 7003 and an inflatable body 2012, also referred herein as an expandable cavity or cavity. FIG. 7B is a cross-sectional view along line D-D of FIG. 7A. The cavity may be bound by the walls of an expandable element defined by walls 7005, for example, like the balloon in FIG. 3B, where walls 7005 can form the structure defined by walls 3013 and 2014. In routing fluids from the multi-lumen catheter tubing 7001, manufacturing challenges arise in sealing the tubings if they are required to traverse through a pressurized element like cavity 2012. A variety of embodiments are provided in the present disclosure. In the first exemplary embodiment, as shown in FIG. 7A, an open lumen of the multi-lumen catheter tubing 7001 can be routed into tube 7002, which traverses the wall 7005 of cavity 2012. This can be implemented by first coating a portion of the outside of tube 7002 with an elastomeric adhesive (such as RTV silicone or other thermoplastic elastomer) and placing it in contact with a dissolvable mold in the shape of the walls 7005 of cavity 2012. The dissolvable mold 7008 is shown in FIG. 7C and FIG. 7D.

Figure 7C:
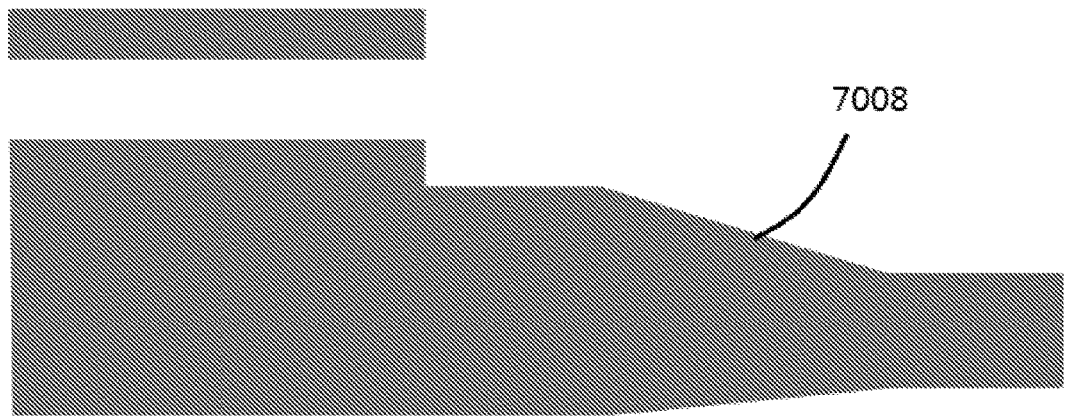
FIG. 7C is a cross-sectional view of a dissolvable mold element used to create the junction in FIG. 7A.
Figure 7D:
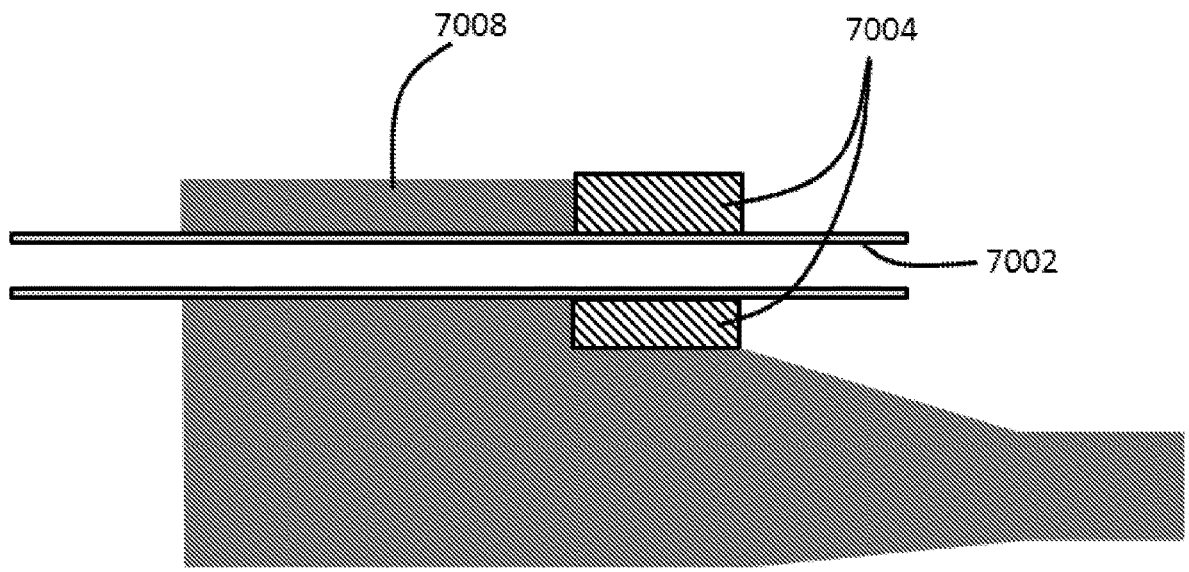
FIG. 7D is an assembly consisting of the dissolvable mold element and tubing used to create the junction in FIG. 7A.

In FIG. 7C, the tubing 7002 has been added in and elastomeric adhesive 7004 has been coated around the outlet junction of tube 7002 and dissolvable mold 7008. Upon coating with a material to form walls 7005 in FIG. 7A (such material may be a vapor deposited polymer such as parylene or may be a dip-coated polymer such as polyimide or the like), the seal around 7002 can be fully formed. Upon removal of the dissolvable mold by common methods of polymer dissolution, the structure formed by walls 7005, tube 7002 and elastomeric material 7004 can be left. Returning to FIG. 7A, this structure may be bonded with adhesive 2007 into the multi-lumen catheter tubing at each tubing junction (7002 to 7001, 7003 to 7001, 7003 to 7005, and 7005 to 7001) to fully form the cavity 2012, which is fluidically isolated from the interior of tubing 7002 and 7003. In the exemplary example where parylene vapor deposition is applied onto RTV adhesive, a strong material bond can be obtained due to the chemical bonds formed during deposition. In this exemplary example, tubes 7002 and 7003 can be made of polyimide, pebax, PEEK, or other common medical plastics. Adhesive 2007 can be cyanoacrylate, light-cured adhesive, or other medical adhesive. Catheter tubing can be comprised of pebax, polyurethane, nylon, or other medical tubing material. Catheter 7001 can be approximately 0.5 to 4 mm in diameter, and tubings 7002 and 7003 can be approximately 0.1 to 2 mm in diameter.

Figure 8:
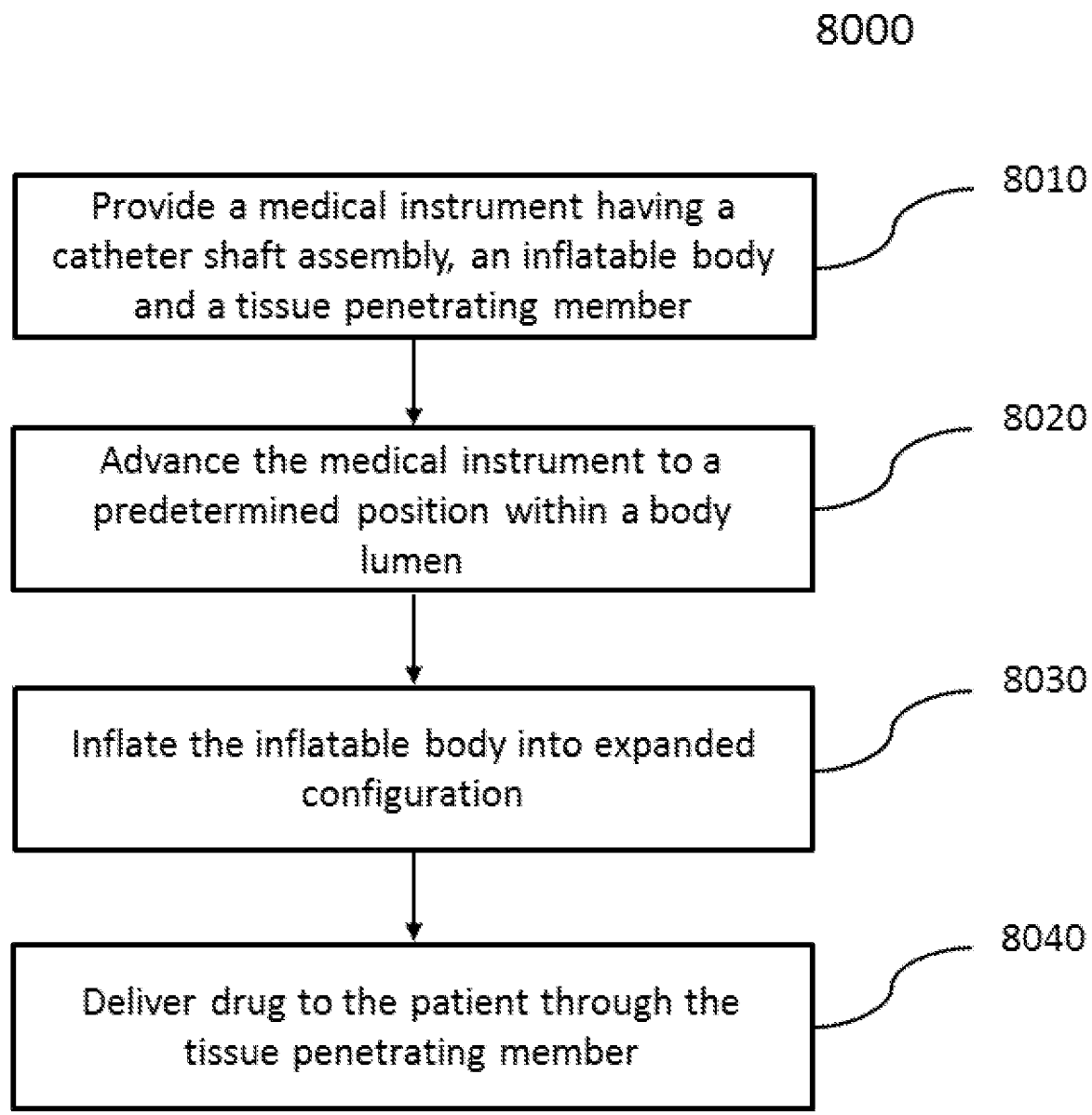
FIG. 8 shows a method for delivering a drug to a patient in accordance with some embodiments of the disclosure.

FIG. 8 shows a method 8000 for delivering a drug to a patient in accordance with some embodiments of the disclosure. The method can be performed to deliver a pharmaceutical drug or a diagnostic agent to a patient's body lumen using the medical instrument for localized drug delivery provided in this disclosure.

In step 8010, a medical instrument as described with reference to FIGS. 1 to 7 of the disclosure can be provided. The medical instrument can comprise a catheter shaft assembly and a hub coupled to a proximal end of the catheter shaft assembly. The catheter shaft assembly can include a catheter body tubing with one or more lumens such as an injection lumen, in inflation lumen and a guidewire lumen. The medical instrument can comprise an inflatable component provided at a distal end of the catheter shaft assembly. The inflatable component can comprise an inflatable body and at least one protective element provided at the inflatable body. The inflatable body can be inflated from an original involuted contracted configuration to a first expanded configuration and then a second expanded configuration as a hydraulic pressure inside the inflatable body gradually increases. At least one tissue penetrating member (e.g., a needle) can be coupled to the inflatable body in an orientation transverse to the longitudinal axis of the catheter shaft assembly. The at least one protective element can be coupled to the inflatable body at a position in proximity to the tissue penetrating member. For instance, the protective element can be placed to surround to the sharp needle tip of the tissue penetrating member and function to protect the inflatable body from needle tip penetration or damage during transit of the medical instrument into and out of the body lumen.

In step 8020, the medical instrument can be advanced over a guidewire to a predetermined position within the body lumen of the patient when the inflatable component is in the involuted contracted configuration. The catheter shaft assembly of the medical instrument can be inserted through an opening in the body or through a percutaneous puncture site of the patient and moved within the patient's body lumen, until a target region is reached. The catheter shaft assembly can be inserted and moved in the body lumen in the involuted contracted configuration where the inflatable body has a minimum profile. During a delivery of the catheter shaft assembly, an imaging technique such as X-ray or magnetic resonance imaging (MRI) can be used to assist in positioning the inflatable body and the tissue penetrating member at the target region. For instance, the protective elements can be radio-opaque to provide feedback on X-ray imaging of the tissue penetrating member tip/inflatable body.

In step 8030, the inflatable component can be inflated into the second expanded configuration when the catheter shaft assembly is at the predetermined position in the body lumen. The hydraulic fluid can be supplied into the inflatable body when the catheter shaft assembly is positioned at the target region, causing the inflatable body to inflate into the first expanded configuration where only the first section of the inflatable body is inflated and then into the second expanded configuration where both the first section and the second section of the inflatable body are inflated to fill the body lumen. In the second expanded configuration, the inflatable body can be fully inflated and the tissue penetrating member can be moved in a direction substantially perpendicular to the axis of the catheter shaft assembly to puncture the wall of the body lumen and advance into the body lumen tissue. In some embodiments, the method for delivering a drug to a patient can further comprise observing an orientation change of the at least one protective element to confirm an inflation of the inflatable body as inflating the inflatable body changes the orientation of the at least one protective element.

In step 8040, the drug can be delivered to the patient through the tissue penetrating member which is in fluid communication with the injection lumen. The tissue penetrating member can be coupled to the injection lumen via the flexible drug line tubing. For instance, the distal end of the flexible drug line tubing proximal to the location that the tissue penetrating member bends upright can be affixed to an exterior surface of the inflatable body, and a shaft end of the tissue penetrating member can be coupled to the distal end of the flexible drug line. Due to a flexibility of the flexible drug line tubing, the distal end of the flexible drug line tubing can be fixed on the exterior surface of the inflatable body during an inflation of the inflatable body, thus the tissue penetrating member is maintained upright with respect to the exterior surface of the inflatable body during an inflation of the inflatable body. Once the drug delivery is completed, the hydraulic fluid can be exhausted from the inflatable body, causing the inflatable body to return to its original, involuted contracted state. The tissue penetrating member can then be either repositioned for further agent delivery or withdrawn from the patient's body lumen.

Although the above steps show method 8000 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial.

Figure 9:
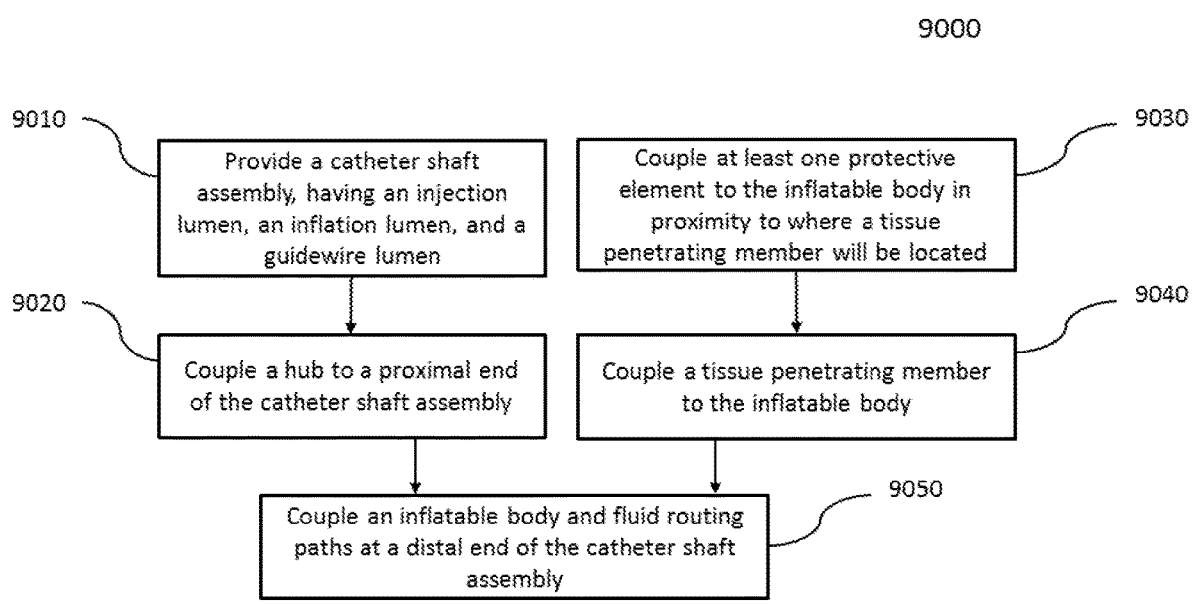
FIG. 9 shows a method for manufacturing a medical instrument for localized drug delivery in accordance with some embodiments of the disclosure.

FIG. 9 shows a method 9000 for manufacturing the medical instrument for localized drug delivery in accordance with some embodiments of the disclosure. In step 9010, a catheter shaft assembly having a proximal end, a distal end, a longitudinal axis between the proximal and distal ends, an injection lumen, an inflation lumen, and a guidewire lumen can be provided. In step 9020, a hub can be coupled to the proximal end of the catheter shaft assembly. The hub can comprise an injection port coupled to the injection lumen, an inflation port coupled to the inflation lumen, and a guidewire port coupled to the guidewire lumen.

In step 9030, at least one protective element can be coupled to the second section in proximity to the tissue penetrating member. At least the tip end of the tissue penetrating member can be bordered by the at least one protective element when the inflatable component is in the involuted contracted configuration. In some embodiments, at least one protective element can be provided at each lateral side of the tissue penetrating member in a cross-sectional view, such that the tissue penetrating member is sheathed and protected by the protective element when the inflatable body is in the involuted contracted configuration. The protective element can function to protect the inflatable body from needle tip penetration or damage during transit of the medical instrument into and out of the body lumen. In some embodiments, the protective elements can be comprised of a hard polymer or metal. The protective elements can be radio-opaque to provide feedback on X-ray imaging of the catheter shaft assembly. Additionally, the pattern/shape of the protective elements can be designed to provide indication on an inflation status of the inflatable body and/or a deployment status of the tissue penetrating member.

In step 9040, a tissue penetrating member can be coupled to the second section of the inflatable component in an orientation transverse to the longitudinal axis of the catheter shaft assembly. The tissue penetrating member can be further coupled to the injection lumen of the catheter shaft assembly. The tissue penetrating member can be coupled to the second section of the inflatable component with a tip end of the tissue penetrating member pointing outwardly of the inflatable component and enclosed within walls of the inflatable component when the inflatable component is in the involuted contracted configuration.

In step 9050, an inflatable component and fluid routing paths can be coupled at the distal end of the catheter shaft assembly. The inflatable component can comprise a first section with a first elasticity and a second section with a second elasticity. As a hydraulic fluid being provided into the inflatable component, the inflatable component can be inflatable from an involuted contracted configuration to a first expanded configuration and further inflatable from the first expanded configuration to a second expanded configuration larger than the first expanded configuration.

Although the above steps show method 9000 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial.

Aspects of the disclosure also provide a medical instrument for localized drug delivery. The medical instrument can comprise a catheter shaft assembly having a proximal end, a distal end, a longitudinal axis between the proximal and distal ends, an injection lumen, and an inflation lumen; a hub coupled to the proximal end of the catheter shaft assembly, the hub comprising an injection port coupled to the injection lumen and an inflation port coupled to the inflation lumen; an inflatable component at the distal end of the catheter shaft assembly, the inflatable component comprising a first section with a first elasticity and a second section with a second elasticity such that the inflatable component is inflatable from an involuted contracted configuration to a first expanded configuration and further inflatable from the first expanded configuration to a second expanded configuration larger than the first expanded configuration; a tissue penetrating member coupled to the second section of the inflatable component in an orientation transverse to the longitudinal axis of the catheter shaft assembly and further coupled to the injection lumen of the catheter shaft assembly, the tissue penetrating member being coupled to the second section of the inflatable component with a tip end of the tissue penetrating member pointing outwardly of the inflatable component and enclosed within walls of the inflatable component when in the involuted contracted configuration; fluid routing paths to connect a catheter shaft assembly to separate fluid pathways integrated into the inflatable component for connections into the pressurized chamber of the inflatable component, the tissue penetrating member, and a guidewire pathway; a torque transmission member coupled to one or more of the distal end of the catheter shaft assembly or the inflatable component; a torqueing element adjacent the distal end of the catheter shaft assembly and coupled to the torque transmission member to transmit torque applied to the torqueing element to one or more of the distal end of the catheter shaft assembly or the inflatable component; and at least one protective element coupled to the first section in proximity to the tissue penetrating member, the at least the tip end of the tissue penetrating member being bordered by the at least one protective element when the inflatable component is in the involuted contracted configuration.

Aspects of the disclosure also provide a method for delivering a drug to a patient. The method comprising providing a medical instrument according to embodiments of the present disclosure; advancing the medical instrument to a predetermined position within a body lumen of the patient when the inflatable component is in the involuted contracted configuration; inflating the inflatable component into the second expanded configuration when the catheter is at the predetermined position in the body lumen; and delivering the drug to the patient through the tissue penetrating member, the tissue penetrating member being in fluid communication with a drug lumen.

Aspects of the disclosure also provide a method of manufacturing medical instrument for localized drug delivery. The method can comprise providing a catheter shaft assembly having a proximal end, a distal end, a longitudinal axis between the proximal and distal ends, an injection lumen, and an inflation lumen; coupling a hub to the proximal end of the catheter shaft assembly, the hub comprising an injection port coupled to the injection lumen and an inflation port coupled to the inflation lumen; coupling an inflatable component at the distal end of the catheter shaft assembly, the inflatable component comprising a first section with a first elasticity and a second section with a second elasticity such that the inflatable component is inflatable from an involuted contracted configuration to a first expanded configuration and further inflatable from the first expanded configuration to a second expanded configuration larger than the first expanded configuration; coupling a tissue penetrating member to the second section of the inflatable component in an orientation transverse to the longitudinal axis of the catheter shaft assembly, and further coupling the tissue penetrating member to the injection lumen of the catheter shaft assembly, the tissue penetrating member being coupled to the second section of the inflatable component with a tip end of the tissue penetrating member pointing outwardly of the inflatable component and enclosed within walls of the inflatable component when in the involuted contracted configuration; coupling a torque transmission member to one or more of the distal end of the catheter shaft assembly or the inflatable component; providing a torqueing element adjacent the distal end of the catheter shaft assembly and coupling the torqueing element to the torque transmission member to transmit torque applied to the torqueing element to one or more of the distal end of the catheter shaft assembly or the inflatable component; and coupling at least one protective element to the first section in proximity to the tissue penetrating member, at least the tip end of the tissue penetrating member being bordered by the at least one protective element when the inflatable component is in the involuted contracted configuration.

While exemplary embodiments are provided where one inflatable body is provided to the medical instruments of the disclosure, it will be appreciated by those in the art that multiple inflatable bodies can be provide to the medical instruments. Alternatively or in combination, one or more successively inflatable bodies can be provided to the medical instruments.

While exemplary embodiments are provided where the medical instruments of the disclosure comprises one inflatable component to deliver drugs/agents to a patient's tissue, it will be appreciated by those in the art that multiple inflatable components can be provided to the medical instruments of this disclosure. The multiple inflatable components can each carry one or more tissue penetrating members. The multiple inflatable components can be connected in series via one same flexible drug line tubing such that the medical instrument of the disclosure can deliver drugs to multiple target regions of the patient. Alternatively or in combination, the multiple inflatable components can be coupled to different injection lumens of the catheter shaft assembly such that a drug delivery through each tissue penetrating member can be individually controlled.

While exemplary embodiments are provided where the medical instruments of the disclosure are used to deliver drugs/agents to a patient's tissue, it will be appreciated by those in the art that the medical instruments of this disclosure can also be used to collect body fluid sample from the patient.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

What is claimed is:

1. A medical instrument for localized drug delivery to tissue, comprising:
   a catheter shaft assembly having a proximal end, a distal end, a longitudinal axis between the proximal and distal ends, at least one injection lumen, at least one inflation lumen, and a guidewire lumen;
   a hub coupled to the proximal end of the catheter shaft assembly, the hub comprising at least one injection port coupled to the at least one injection lumen, at least one inflation port coupled to the at least one inflation lumen, and a guidewire port coupled to the guidewire lumen;
   an inflatable body at the distal end of the catheter shaft assembly, the inflatable body being inflatable from an involuted contracted configuration;
   a tissue penetrating member coupled to the inflatable body in an orientation transverse to the longitudinal axis of the catheter shaft assembly and further coupled to the at least one injection lumen of the catheter shaft assembly, wherein said tissue penetrating member is coupled to the inflatable body with a tip end of said tissue penetrating member pointing outwardly of the inflatable body and enclosed within a wall of the inflatable body when in the involuted contracted configuration; and at least one protective element coupled to said inflatable body in proximity to said tissue penetrating member, wherein at least the tip end of said tissue penetrating member is bordered by said at least one protective element when said inflatable body is in said involuted contracted configuration, wherein said at least one protective element is radio-opaque and is configured to provide an indication of an inflation status of said inflatable body when viewed via x-ray, wherein said tissue penetrating member is in fluidic communication with a flexible drug line tubing, and said flexible drug line tubing is routed through the wall of the inflatable body by passing through a junction of elastomeric material coated with parylene.

2. The medical instrument of claim 1, wherein said at least one inflation port is coupled to a pressure release valve configured to regulate a pressure of a hydraulic fluid.

3. The medical instrument of claim 1, further comprising a labeling showing at least a parameter of said medical instrument.

4. The medical instrument of claim 3, wherein said labeling is provided at an injunction of the hub and the catheter shaft assembly.

5. The medical instrument of claim 1, wherein a distal end of said flexible drug line tubing is in fluidic communication to the tissue penetrating member and is affixed to an exterior surface of the inflatable body.

6. The medical instrument of claim 1, wherein the at least one protective element is provided on each lateral side of said tissue penetrating member when said inflatable body in the involuted contracted configuration.

7. The medical instrument of claim 1, wherein the inflatable body comprises a first section with a first elasticity and a second section with a second elasticity.

8. The medical instrument of claim 7, wherein the inflatable body is inflatable from the involuted contracted configuration to a first expanded configuration and further inflatable from the first expanded configuration to a second expanded configuration larger than the first expanded configuration.

9. The medical instrument of claim 1, wherein said at least one protective element is provided with a specific pattern or shape.

10. The medical instrument of claim 9, wherein the specific pattern or shape is asymmetric to indicate said inflation status of the inflatable body.

11. The medical instrument of claim 1, wherein said at least one protective element is integrated with the inflatable body.

12. The medical instrument of claim 1, further comprising a torque transmission tube having an axis parallel to the axis of the catheter shaft assembly, the torque transmission tube transmitting a torque from the proximal end of the catheter shaft assembly to the distal end of the catheter shaft assembly.

13. The medical instrument of claim 12, wherein the torque transmission tube is comprised of a stainless steel hypodermic tubing that is cut in a pattern to allow a transmission of torque while removing a bending stiffness of the torque transmission tube.

14. The medical instrument of claim 12, wherein the torque transmission tube is coupled to one or more of the distal end of the catheter shaft assembly or the inflatable body.

15. The medical instrument of claim 12, wherein the torque transmission tube is proximally fixed to a torqueing element.

16. The medical instrument of claim 1, wherein said tissue penetrating member is in fluidic communication with said at least one injection lumen.

17. A medical instrument for localized drug delivery to tissue,
comprising
a catheter shaft assembly having a proximal end, a distal end, a longitudinal axis between the proximal and distal ends, at least one injection lumen, and at least one inflation lumen;
a hub coupled to the proximal end of the catheter shaft assembly, the hub comprising an injection port coupled to the at least one injection lumen and an inflation port coupled to the at least one inflation lumen;
an inflatable body at the distal end of the catheter shaft assembly, the inflatable body being inflatable from an involuted contracted configuration;
a tissue penetrating member coupled to said inflatable body in an orientation transverse to the longitudinal axis of the catheter shaft assembly and further coupled to the at least one injection lumen of the catheter shaft assembly, wherein said tissue penetrating member is coupled to the inflatable body with a tip end of said tissue penetrating member pointing outwardly of the inflatable body and enclosed within a wall of the inflatable body when in the involuted contracted configuration;
a torque transmission member coupled to one or more of the distal end of the catheter shaft assembly or the inflatable body;
a torqueing element adjacent the proximal end of the catheter shaft assembly and coupled to the torque transmission member to transmit torque applied to the torqueing element to one or more of the distal end of the catheter shaft assembly or the inflatable body; and
at least one protective element coupled to said first section in proximity to said tissue penetrating member, wherein at least the tip end of said tissue penetrating member is bordered by said at least one protective element when said inflatable body is in said involuted contracted configuration, wherein said at least one protective element is radio-opaque and is configured to provide an indication of an inflation status of said inflatable body when viewed via x-ray,
wherein said tissue penetrating member is in fluidic communication with a flexible drug line tubing, and said flexible drug line tubing is routed through the wall of the inflatable body by passing through a junction of elastomeric material coated with parylene.

18. The medical instrument of claim 17, wherein said inflation port is coupled to a pressure release valve configured to regulate a pressure of a hydraulic fluid.

19. The medical instrument of claim 17, further comprising a labeling showing at least a parameter of said medical instrument.

20. A medical instrument for localized drug delivery to tissue, comprising:
- a catheter shaft assembly having a proximal end, a distal end, a longitudinal axis between the proximal and distal ends, at least one injection lumen, at least one inflation lumen, and a guidewire lumen;
- a hub coupled to the proximal end of the catheter shaft assembly, the hub comprising at least one injection port coupled to the at least one injection lumen, at least one inflation port coupled to the at least one inflation lumen, and a guidewire port coupled to the guidewire lumen;
- an inflatable body at the distal end of the catheter shaft assembly, the inflatable body is inflatable from an involuted contracted configuration;
- a tissue penetrating member coupled to the inflatable body in an orientation transverse to the longitudinal axis of the catheter shaft assembly and further coupled to the at least one injection lumen of the catheter shaft assembly, wherein said tissue penetrating member is coupled to the inflatable body with a tip end of said tissue penetrating member pointing outwardly of the inflatable body and enclosed within a wall of the inflatable body when in the involuted contracted configuration; and
- a fluid routing tube coupled through the wall of the inflatable body by means of an elastomeric joint coated with parylene and connected at its proximal end to the at least one injection lumen within the catheter shaft assembly and connected at its distal end to the tissue penetrating member.

21. The medical instrument of claim 20, wherein said at least one inflation port is coupled to a pressure release valve configured to regulate a pressure of a hydraulic fluid.

22. The medical instrument of claim 20, further comprising at least one protective element coupled to the inflatable body in proximity to said tissue penetrating member, wherein at least the tip end of said tissue penetrating member is bordered by said at least one protective element when said inflatable body is in said involuted contracted configuration.

23. The medical instrument of claim 22, wherein said at least one protective element is provided with a specific pattern or shape.

24. The medical instrument of claim 23, wherein the specific pattern or shape is asymmetric to indicate an inflation status of the inflatable body.

25. The medical instrument of claim 20, further comprising a labeling showing at least a parameter of said medical instrument.

26. The medical instrument of claim 20, wherein said fluid routing tube is flexible.

27. The medical instrument of claim 26, wherein a distal end of said fluid routing tube is in fluidic communication to the tissue penetrating member and is affixed to an exterior surface of the inflatable body.

28. The medical instrument of claim 20, further comprising a torque transmission tube having an axis parallel to the axis of the catheter shaft assembly, the torque transmission tube transmitting a torque from the proximal end of the catheter shaft assembly to the distal end of the catheter shaft assembly.

* * * * *